(12) United States Patent
Villata et al.

(10) Patent No.: US 7,857,113 B2
(45) Date of Patent: Dec. 28, 2010

(54) HYDRAULIC CLUTCH CONTROL SYSTEM, COMPRISING SERVO MEANS WHICH ARE DISPOSED BETWEEN THE MASTER CYLINDER AND THE SLAVE CYLINDER OF THE SYSTEM

(75) Inventors: Gino Villata, Buttigliera D'Asti (IT); Pascal Thery, Amiens (FR)

(73) Assignee: Valeo Embrayages, Amiens Cedex (FR)

( * ) Notice: Subject to any disclaimer, the term of this patent is extended or adjusted under 35 U.S.C. 154(b) by 947 days.

(21) Appl. No.: 10/576,371

(22) PCT Filed: Nov. 8, 2004

(86) PCT No.: PCT/FR2004/050573

§ 371 (c)(1),
(2), (4) Date: Jan. 18, 2007

(87) PCT Pub. No.: WO2005/047722

PCT Pub. Date: May 26, 2005

(65) Prior Publication Data

US 2007/0205072 A1  Sep. 6, 2007

(30) Foreign Application Priority Data

Nov. 12, 2003  (FR) .................................. 03 50826

(51) Int. Cl.
*F15B 7/06*  (2006.01)
*F16D 23/12*  (2006.01)
*F16D 48/02*  (2006.01)

(52) U.S. Cl. ..................... 192/85.6; 192/85.59; 60/574; 60/579

(58) Field of Classification Search .................. 60/574, 60/591, 560, 579; 192/85.56, 85.6, 85.59
See application file for complete search history.

(56) References Cited

U.S. PATENT DOCUMENTS

| 1,951,224 A | * | 3/1934 | Von Oberstadt ............... 60/574 |
| 2,321,479 A | * | 6/1943 | Freeman ...................... 188/347 |
| 3,200,597 A | * | 8/1965 | Stotz ............................ 60/594 |
| 3,630,027 A | * | 12/1971 | Lambert ....................... 60/563 |
| 3,752,282 A | * | 8/1973 | Espenshied ............... 192/91 R |
| 3,812,766 A |   | 5/1974 | Weiss |
| 4,378,676 A | * | 4/1983 | Parsons et al. ................ 60/548 |
| 4,821,518 A | * | 4/1989 | Coupland et al. ............. 60/579 |
| 5,127,506 A | * | 7/1992 | Muller et al. ............. 192/85 C |

(Continued)

FOREIGN PATENT DOCUMENTS

DE  19509356 A1  9/1996

(Continued)

*Primary Examiner*—David D Le
*Assistant Examiner*—Terry Chau
(74) *Attorney, Agent, or Firm*—Berenato & White, LLC

(57) ABSTRACT

The invention relates to a system for the hydraulic control (10) of a clutch (12), e.g. a motor vehicle clutch, comprising an upstream master cylinder (14) which is connected to a down-stream slave cylinder (18) by means of a conduit (16). The invention is characterized in that the system comprises a servo cylinder (30) which is disposed in the conduit (16) between the master cylinder (14) and the slave cylinder (18), said servo cylinder comprising at least one servo piston which can be subjected to an assist force produced by a servo device.

16 Claims, 13 Drawing Sheets

U.S. PATENT DOCUMENTS

| | | | | |
|---|---|---|---|---|
| 5,279,204 | A | * | 1/1994 | Arnold .................. 91/376 R |
| 5,301,781 | A | * | 4/1994 | Tischer et al. ............ 192/85 R |
| 5,809,830 | A | | 9/1998 | Chazot |
| 5,970,817 | A | * | 10/1999 | Ichiba ..................... 74/512 |
| 6,435,327 | B1 | * | 8/2002 | Rohs et al. ............... 192/85 R |

FOREIGN PATENT DOCUMENTS

| | | |
|---|---|---|
| DE | 19717486 A1 | 10/1998 |
| GB | 2236153 A | 3/1991 |
| GB | 2313885 A | 12/1997 |

* cited by examiner

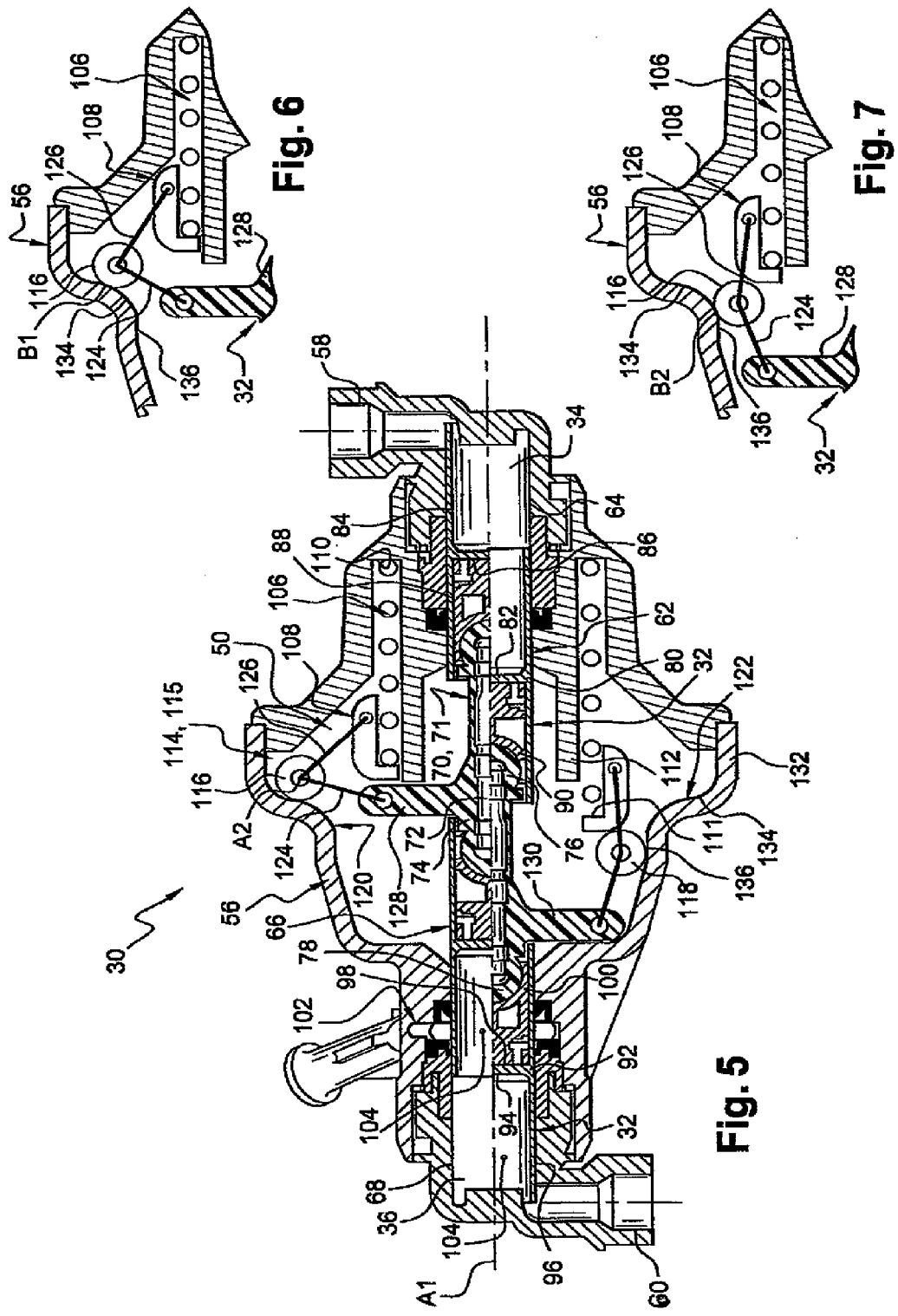

HYDRAULIC CLUTCH CONTROL SYSTEM, COMPRISING SERVO MEANS WHICH ARE DISPOSED BETWEEN THE MASTER CYLINDER AND THE SLAVE CYLINDER OF THE SYSTEM

BACKGROUND OF THE INVENTION

1. Field of the Invention.

The invention concerns a system for the hydraulic control of a clutch.

The invention concerns more particularly a system for the hydraulic control of a clutch, in particular for a motor vehicle, comprising an upstream sending cylinder connected by a conduit to a downstream receiving cylinder so as to form a hydraulic control circuit.

2. Description of the Related Art.

It is sometimes desirable to equip the hydraulic control system for a clutch with an assistance device so as to minimise the force that the user has to apply to the clutch control pedal during the declutching phase.

Such a device is described for example in the document US-B-6.213.271.

In this document, the assistance device is mounted on the sending cylinder of the hydraulic clutch control system.

This system has the drawback of requiring a specific sending cylinder adapted to the arrangement of the supplementary elements fulfilling the assistance function.

The arrangement of the supplementary elements on the sending cylinder poses problems of space requirements and this makes the sending cylinder more complex to produce.

SUMMARY OF THE INVENTION

The present invention aims to remedy these drawbacks by proposing a simple and economical solution that does not require modifying the sending cylinder or receiving cylinder.

For this purpose, the invention proposes a control system of the type described above, characterised in that it comprises an assistance cylinder that is interposed in the conduit, between the sending cylinder and the receiving cylinder, and which comprises at least one assistance piston that is mounted so as to slide axially in the body of the assistance cylinder between an upstream engagement position and a downstream disengagement position, so as to delimit an upstream hydraulic chamber and a downstream hydraulic chamber with variable volumes according to the axial position of the piston, the upstream chamber being connected to the sending cylinder by a portion of hydraulic circuit referred to the upstream circuit and the downstream chamber being connected to the receiving cylinder by a portion of the hydraulic circuit referred to as the downstream circuit, each hydraulic circuit portion comprising a means of relevelling the volume of fluid connected to at least one fluid reservoir, and in that the assistance cylinder comprises an assistance device that applies an assistance force to the assistance piston during the declutching phase.

One advantage of the system according to the invention is that it uses a sending cylinder and receiving cylinder of a standard type, which have not been designed to be equipped with an assistance device.

In addition, the clutch control system according to the invention can be arranged in a vehicle without its being necessary to modify the area where the sending cylinder is arranged and/or the area where the receiving cylinder is arranged, compared with a similar vehicle not equipped with the assistance device, the space requirement of the sending cylinder and the space requirement of the receiving cylinder not being modified.

Another advantage of the control system according to the invention is that the assistance cylinder and its assistance device do not have any influence on the control law linking the movement of the clutch control pedal to the movement to the movement of the clutch diaphragm. The position of the diaphragm is therefore always dependent on the position of the pedal.

Yet another advantage of the control system according to the invention is that, as the two upstream and downstream circuits have a means of relevelling the volume of fluid, the system keeps a constant operating point whatever the variations in the position of the clutch, variations which may stem for example from wear on the clutch, heating thereof, or the control of the clutch.

According to other characteristics of the invention:

- the assistance device comprises a regulation means which makes the value of the assistance force vary according to the travel of the clutch control pedal in accordance with a predetermined assistance law;
- the assistance device comprises a transmission member which transmits the assistance force to the assistance piston;
- the transmission member is connected in terms of axial movement to the assistance piston in both directions of sliding of the piston;
- the transmission member cooperates by contact with an associated abutment surface of the assistance piston so that, in the case where the speed of the assistance device is less than the speed of the assistance piston, the assistance device does not slow down the sliding of the assistance piston towards the downstream end;
- the transmission member is arranged at an axial end of the assistance piston;
- the piston comprises an upstream portion that delimits the upstream chamber and a downstream portion that delimits the downstream chamber, the two portions being connected in axial movement by a connecting rod, and the connecting rod constitutes the transmission member of the assistance device;
- the hydraulic circuit being connected to a fluid reservoir in the engagement position, the assistance cylinder comprises at least one discharge orifice which makes at least one hydraulic chamber communicate with the fluid reservoir, when the assistance piston is occupying its upstream position, so as to compensate for the variations in hydraulic volume in the hydraulic circuit over time;
- the discharge orifice is arranged in the assistance piston and the discharge orifice makes the upstream chamber communicate with the downstream chamber, when the assistance piston is occupying its upstream position;
- the discharge orifice comprises a valve that is controlled by the axial movement of the assistance piston;
- the assistance device comprises an elastic element which stores energy during the engagement phase and which restores the energy during the disengagement phase in order to produce the assistance force;
- the regulation means is a cam mechanism which is driven by the axial movement of the piston and which regulates the assistance force produced by the elastic element during the disengagement phase;
- the assistance device is housed in the cylinder body and the cam mechanism comprises at least one control surface that is produced on an internal wall of the cylinder body;

the elastic assistance element is an axial compression elastic element that is interposed axially between a cup and an abutment surface fixed with respect to the assistance cylinder body, the cam mechanism comprises at least one movable roller which travels over a control surface between an upstream position and a downstream position corresponding respectively to the upstream and downstream positions of the assistance piston, and the movable roller is connected by a first connecting rod to the piston by a second connecting rod to the cup;

the axis by which the connecting rods pivot on the movable roller is concurrent with the rotation axis of the roller;

the control surface comprises an upstream portion inclined with respect to the sliding axis, and a downstream portion roughly parallel to the sliding axis so that, during a first part of the disengagement phase, the movable roller moves first of all on the inclined portion towards the axis and in the downstream direction, from its upstream position, transmitting part of the relaxation force of the elastic assistance element to the assistance piston, by a step-down effect, and then, during a second part of the disengagement phase, the movable roller moves on the downstream portion in the downstream direction, in a roughly axial direction, transmitting all the relaxation force of the elastic assistance element to the assistance piston;

the distance between the pivot axes of the second connecting rod is such that, in the upstream position of the movable roller, the roller moves in the upstream direction beyond the point on the control surface where the second connecting rod is perpendicular to the control surface, so that the expansion force of the elastic assistance element biases the movement roller towards its upstream position;

the axial dimension of the elastic assistance force in the relaxed state is less than the axial distance between the cup and the associated fixed abutment surface, when the piston occupies its downstream position, so as to suspend the assistance force during the end of the travel of the piston in the downstream direction;

the assistance device comprises an electrical actuator that controls the relaxation of the elastic element during the disengagement phase;

the means of regulating the assistance device is an electronic control unit that controls the electrical actuator;

the elastic assistance element is a helical compression spring;

the assistance device is connected to an energy source that is external to the control system and that is installed in the vehicle that the control system equips, and the said energy produces the assistance force that is transmitted to the piston;

the assistance device comprises an electrical actuator controlled so as to transmit an assistance force to the piston during the disengagement phase;

the means of regulating the assistance device is an electronic control unit that controls the electrical actuator producing the assistance force;

the assistance device comprises a ram that is connected to a hydraulic or pneumatic pressure source and that transmits an assistance force to the piston during the disengagement phase;

the means of regulating the assistance device comprises at least one control valve interposed between the ram and the hydraulic or pneumatic pressure source;

the regulation means comprises a two-position control valve connected to a pressure source in order to form a charging valve and a two-position control valve connected to a fluid reservoir in order to form a discharge valve, and each control valve is controlled by the hydraulic pressure in the upstream circuit, so that the hydraulic pressure in the upstream circuit tends towards a first constant value during a disengagement travel and tends towards a second constant value, less than the first value, during an engagement travel;

the regulation means comprises a three-position control valve, a charging position that is connected to a pressure source, an intermediate closure position, and a discharge position connected to a fluid reservoir, and the control valve is controlled, on the charging position side, by the hydraulic pressure in the upstream circuit and, on the discharge position side, by the hydraulic pressure in the downstream circuit, so that the assistance force applied to the assistance piston during the disengagement phase is proportional to the hydraulic pressure in the downstream circuit;

the distributor is controlled by an electronic control unit;

the piston comprises at least one elastic element that returns the piston towards its upstream position.

BRIEF DESCRIPTION OF THE DRAWINGS

Other characteristics and advantages of the invention will emerge from a reading of the following detailed description, for an understanding of which reference will be made to the accompanying drawings, in which:

FIG. 5 is a view in axial section depicting schematically the assistance of the control system according to a first embodiment of the invention in which the assistance device comprises a cam mechanism, the piston being shown respectively in its upstream position and in its downstream position;

FIGS. 6 and 7 are partial views in axial section which depict a detail of FIG. 5 and which illustrate two successive intermediate positions of a movable roller equipping the cam mechanism;

DETAILED DESCRIPTION OF THE PREFERRED EMBODIMENTS

In the following description, identical, similar or analogous elements will be designated by the same reference numbers.

Figure 1:
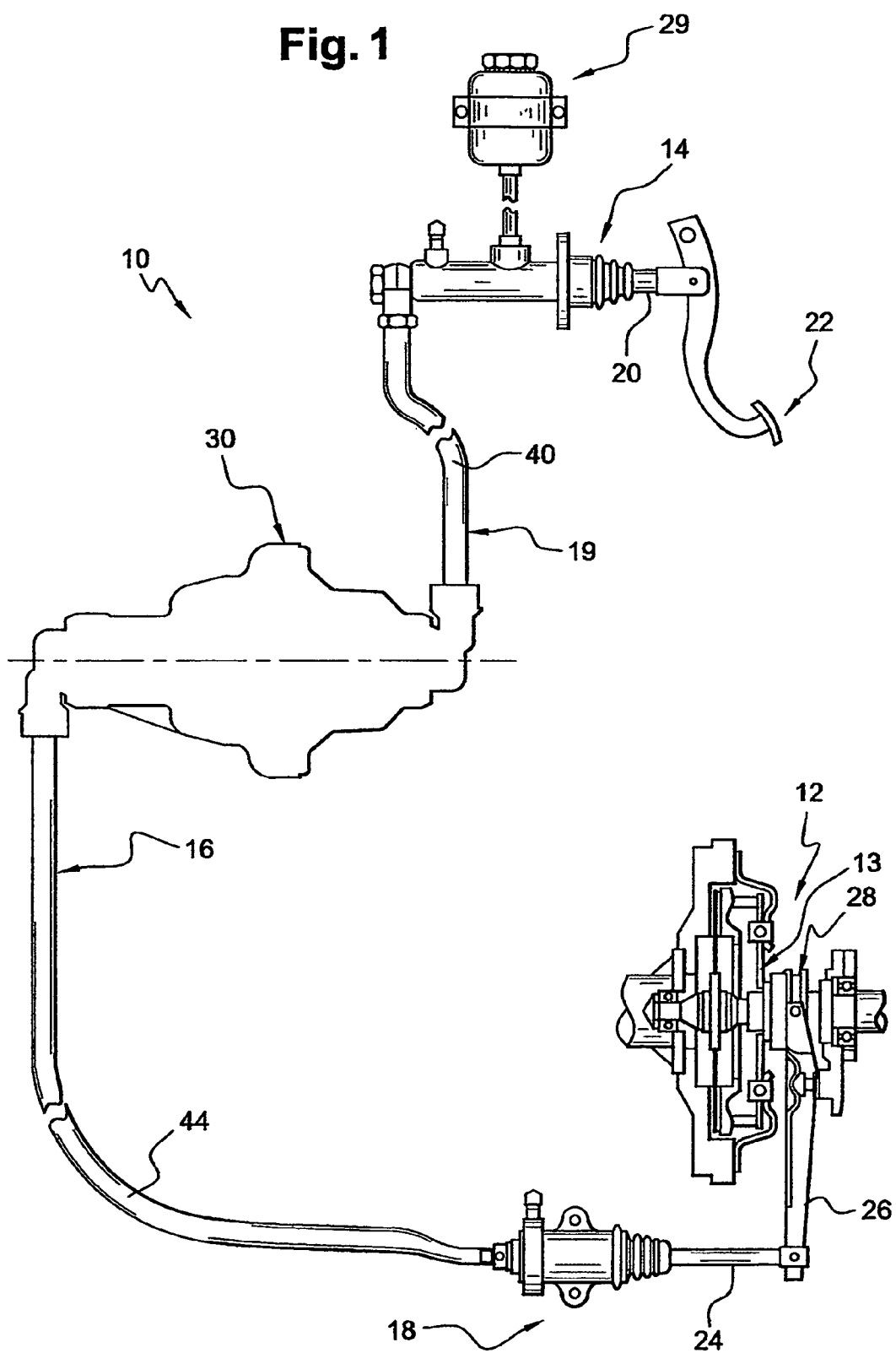
FIG. 1 is a diagram representing a hydraulic clutch control system produced in accordance with the teachings of the invention.

FIG. 1 depicts a hydraulic control system 10 of a motor vehicle clutch 12 produced in accordance with the teachings of the invention.

The control system 10 comprises an upstream sending cylinder 14 connected by a pipe or conduit 16 to a downstream receiving cylinder 18 with a similar structure to the sending cylinder 14.

The sending cylinder 14, the receiving cylinder 18 and the conduit 16 form a hydraulic control circuit 19.

Each sending 14 or receiving 18 cylinder comprises a piston (not shown) able to move axially inside a cylinder body in order to delimit a hydraulic chamber of variable volume. A connection orifice, to which the conduit 16 is connected, opens out in the hydraulic chamber.

The sending cylinder 14 comprises a piston rod 20 connected here to a clutch pedal 22 on which the driver of the vehicle acts.

The piston of the sending cylinder 14 is designed to expel a control fluid or liquid contained in the hydraulic chamber in the direction of the conduit 16, during a declutching operation.

When the clutch 12 is engaged, the volume of the hydraulic chamber of the sending cylinder 14 is at a maximum whilst the volume of the hydraulic chamber of the receiving cylinder 18 is at a minimum.

During the declutching operation, the volume of the hydraulic chamber of the sending cylinder 14 decreases, whilst the volume of the hydraulic chamber of the receiving cylinder 18 increases.

The piston of the receiving cylinder 18 then causes the movement of a rod 24, which acts here on a declutching fork 26 actuating a clutch release bearing 28.

When the driver releases his action on the clutch pedal 22, the piston of the receiving cylinder 18 is returned towards its initial position by a clutch spring such as a diaphragm 13.

In returning to its initial position, the receiving cylinder 18 pushes the column of oil contained in the hydraulic circuit 19, which causes the return of the piston of the sending cylinder 14 to its initial position.

The clutch pedal 22 is returned to its initial position by a return spring and/or by the return of the piston of the sending cylinder 14.

Generally, each sending 14 and receiving 18 cylinder comprises a spring (not shown) which acts between the piston and the bottom of the body of the cylinder, and which guarantees the return of the piston as far as its initial position in abutment.

Preferably, the hydraulic chamber of the sending cylinder 14 is able to be connected to a fluid reservoir 29, so as to compensate for the variations in volume of the hydraulic circuit 19 over time.

To this end, the hydraulic chamber of the sending cylinder 14 comprises at least one discharge orifice (not shown) which is open when the sending piston returns completely to its initial position and which makes the hydraulic circuit 19 communicate with the reservoir 29.

It should be noted that, during the declutching phase, the pedal 22 has dead travel at the start of its pivoting, which corresponds to a movement of the sending piston as far as the axial position in which it closes the discharge orifice.

During the dead travel, the sending piston pushes the fluid towards the reservoir 29, without causing the movement of the receiving piston.

In accordance with the teachings of the invention, the control system 10 comprises an assistance cylinder 30 interposed in the conduit 16, between the sending cylinder 14 and the receiving cylinder 18.

Figure 2:
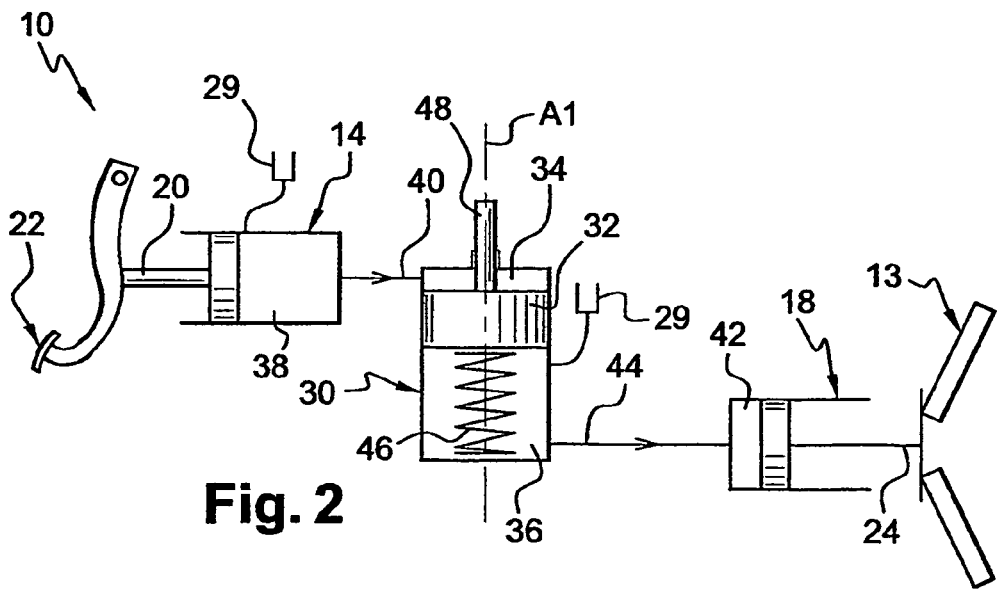
FIGS. 2 and 3 illustrate schematically the operating principle of the assistance in the control system according to the invention.

FIG. 2 depicts the control system 10 according to the invention in an simplified manner.

It should be noted that, in this figure, the rod 24 of the receiving piston acts directly on the diaphragm 13 of the clutch 12 by means of a bearing comprising a ball bearing (not shown).

The assistance cylinder 30 comprises an assistance piston 32 mounted so as to slide along a principal axis A1, between an upstream position and a downstream position, so as to delimit an upstream hydraulic chamber 34 and a downstream hydraulic chamber 36 with variable volumes according to the axial position of the piston 32.

The upstream chamber 34 communicates with the chamber 38 of the sending cylinder 14 by means of an upstream portion 40 of the hydraulic circuit 19, and the downstream chamber communicates with the chamber 42 of the receiving cylinder 18 by means of a downstream portion 44 of the hydraulic circuit 19.

The upstream hydraulic circuit 40 is connected to the fluid reservoir 29 at the sending chamber 38.

The downstream hydraulic circuit 44 is connected to a fluid reservoir, for example the same reservoir 29 as the upstream hydraulic circuit 40, here at the downstream chamber 36 of the assistance cylinder 30.

According to the embodiment illustrated here, the assistance cylinder 30 comprises a spring 46 which is interposed axially between the assistance piston 32 and the bottom of the downstream chamber 36, and which returns the assistance piston 32 towards its upstream position.

In the diagram, the assistance piston 32 comprises a rod 48 which extends towards the outside through the upstream chamber 34.

According to a variant (not shown), the assistance cylinder 30 with its piston 32 can be replaced by a chamber comprising an intermediate membrane separating the upstream 34 and downstream 36 chambers and fulfilling the role of the assistance piston 32. This membrane in the same way comprises the rod 48.

Figure 3:
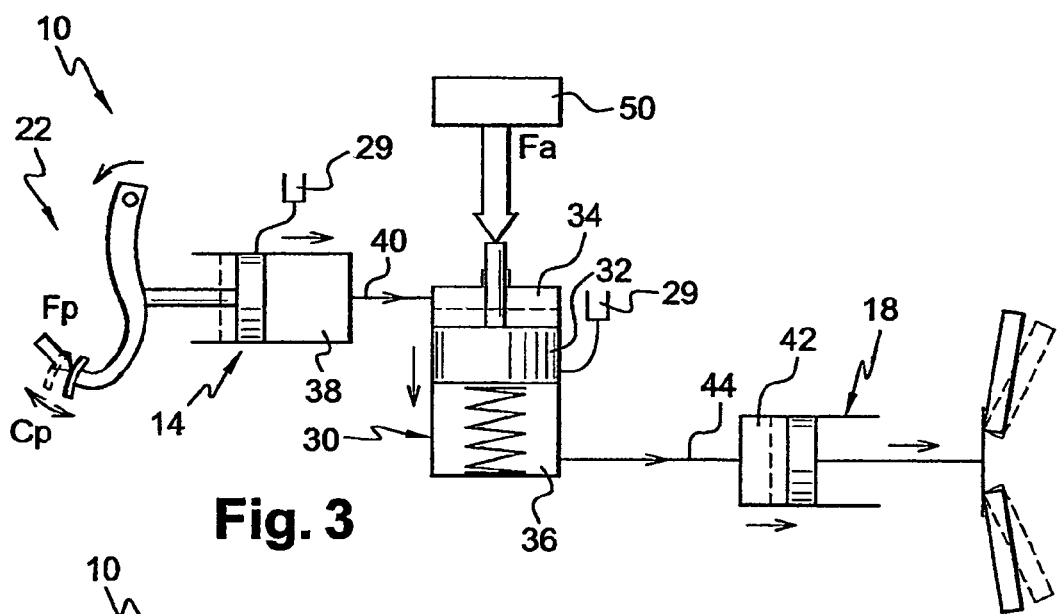

In accordance with the teachings of the invention, during the declutching phase, which is illustrated by FIG. 3, an assistance force $F_a$ is applied to the assistance piston 32, here by means of the rod 48, so as to relieve the abutment force $F_p$ of the user on the pedal 22.

The assistance force $F_a$ is produced by an assistance device 50 which will be described hereinafter.

Figure 4:
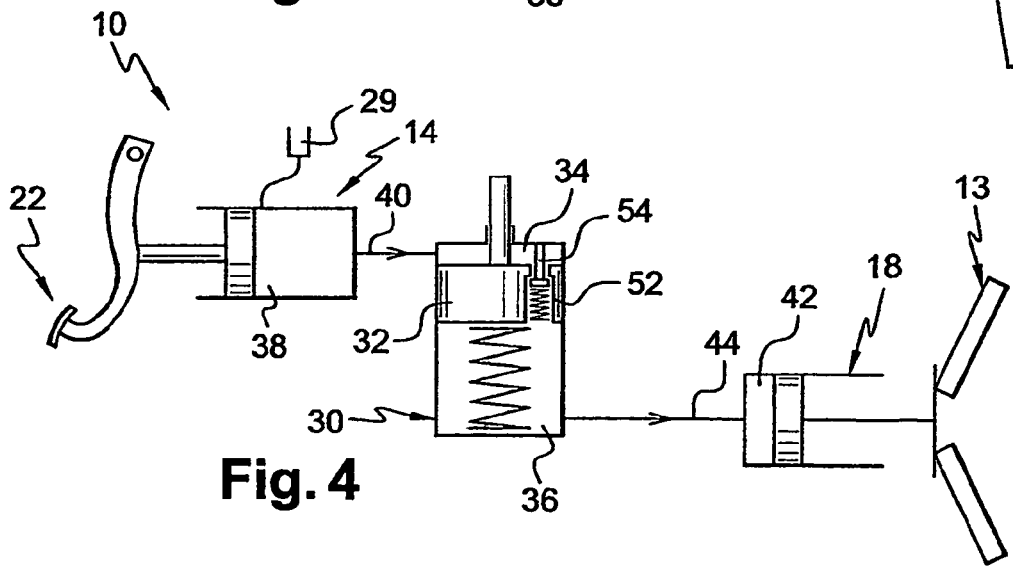
FIG. 4 is a diagram similar to that of FIG. 2 that illustrates a variant embodiment of the dumping to reservoir of the hydraulic control circuits.

According to a variant embodiment depicted in FIG. 4, a discharge orifice 52 is produced in the assistance piston 32, so as to make the upstream hydraulic circuit 40 communicate with the downstream hydraulic circuit 44 when the piston 32 is occupying its upstream position.

According to the diagram in FIG. 4, the discharge orifice 32 passes axially through the piston 32 and comprises a discharge valve 54 which is biased elastically towards its closure position and which opens mechanically when the assistance piston 32 comes to occupy its upstream position, by the abutment of a rod of the valve 42 on the bottom of the upstream chamber 34.

The arrangement of the discharge orifice 52 in the piston 32 makes it possible in particular to connect the entire hydraulic circuit 19 to the fluid reservoir 29, with a single connection, arranged here at the sending cylinder 14.

This arrangement also makes it possible not to add additional dead travel to the clutch pedal 22, which is the case when the assistance cylinder 30 is connected to the reservoir 29 as in FIG. 2.

The opening of the discharge valve 54 can be calibrated so that an abrupt increase in the hydraulic pressure in the sending chamber 38 causes, almost immediately, a movement of the assistance piston 32 in the downstream direction, the fluid not having the time to flow through the discharge valve 34, and therefore the closure of the discharge orifice 52. This calibration can make it possible to choose the value of the first axial travel of the assistance piston 32 in the downstream direction, before the assistance device 50 has begun to apply an assistance force $F_a$.

A description is now given of a first embodiment of the control system 10 according to the invention which is shown in FIGS. 5 to 7, in which the assistance device 50 comprises an elastic element which stores energy during the engagement phase and which restores the energy, in the form of an assistance force $F_a$, during the disengagement phase.

According to the first embodiment, the assistance cylinder 30 comprises a cylinder body 56 which is provided with an inlet orifice 58 and a discharge orifice 60.

The assistance piston 32 is mounted so as to slide, along the principal axis A1 within the cylinder body 56, which has roughly a tubular shape of axis A1.

In the remainder of the description, elements will be termed internal or external with respect to the principal axis A1 in a radial direction.

Considering FIG. 5, the piston 32 is shown in the upstream position on the top half section and in the downstream position on the bottom half section.

The upstream chamber 34 communicates with the sending cylinder 14 through the inlet orifice 58, and the downstream chamber 36 communicates with the receiving cylinder 18 through the discharge orifice 60.

According to the embodiment depicted here, the assistance piston 32 is produced in several parts.

The piston 32 comprises an upstream portion 62, which is designed to slide axially in a complementary upstream bore 64, and a downstream portion 66 which is designed to slide axially in a complementary downstream bore 68, the two portions 62, 66 being connected with respect to axial movement by an axial connecting rod 70.

The connecting rod 70 comprises here an internal rod 72, for example made from metal, and an external body 74 moulded onto the internal rod 72.

The upstream end 76 and the downstream end 78 of the rod 70 are each here in the form of a spherical head.

The two portions 62, 66 here have roughly identical shapes.

The upstream portion 62 has overall a tubular shape with an H-shaped axial profile, that is to say it has two tubular parts substantially symmetrical with respect to a transverse separation wall 80.

On the side of the upstream face 82 of the transverse wall 80, the upstream portion 62 forms a jacket 84 which delimits a part of the upstream chamber 34.

On the side of the downstream face 86 of the transverse wall 80, the upstream portion 62 forms a housing 88 which receives a roughly cylindrical piece 90 forming a receptacle for the connection between the upstream axial end 76 of the connecting rod 70 and the upstream portion 62 of the piston 32.

According to the embodiment depicted here, the downstream portion 66 is substantially similar to the upstream portion 62 and the downstream portion 66 is arranged substantially symmetrically with the upstream portion 62, with respect to a transverse symmetry plane.

Thus the downstream portion 66 has a transverse separation wall 92 and, on the side of the downstream face 94 of this wall 92, forms a jacket 96 which delimits a part of the downstream chamber 36.

On the side of the upstream face 98 of the transverse wall 92, the downstream portion 66 receives a cylindrical piece 100, similar to that of the upstream portion 62, forming a receptacle for the connection between the downstream axial end 78 of the connecting rod 70 and the downstream portion 66.

In the embodiment shown, the downstream bore 68 has an annular radial groove 102 which communicates with the liquid reservoir 29, so as to form a discharge orifice.

This embodiment therefore corresponds to the embodiment depicted in FIGS. 2 and 3, in which the downstream circuit 44 comprises a connection to the reservoir 29 at the downstream chamber 36.

The jacket 96 of the downstream portion 66 comprises here several radial orifices 104 which are substantially aligned circumferentially and which are arranged opposite the radial groove 102, when the piston 32 occupies its upstream position, as depicted in the top half of FIG. 5.

The radial orifices 104 make it possible to put the downstream chamber 36 and the reservoir 29 in communication, when the piston 32 is occupying its upstream position, so as to compensate for the variations in hydraulic volume in the downstream circuit 44 over time.

In the downstream position of the piston 32, as depicted in the bottom half of FIG. 5, the orifices 104 are offset axially in the downstream direction, with respect to the radial groove 102, so that the downstream chamber 36 does not communicate with the reservoir 29.

Naturally, as indicated with reference to the variant in FIG. 4, the radial groove 102 and the radial orifices 104 can be omitted in favour of a discharge orifice 52 produced axially in the piston 32 and provided with a discharge valve 54.

The assistance device 50 comprises here an elastic element in the form of an axial helical compression spring 106.

The spring 106 is designed to compress during the engagement phase, under the effect of the return of the assistance piston 32 to its upstream position, so as to store energy, and is designed to restore this energy during the disengagement phase, producing an assistance force $F_a$.

The spring 106 is interposed axially between an axially movable annular cup 108 and a fixed annular radial abutment surface 110 provided in the cylinder body 56.

The cup 108 comprises an annular radial abutment surface 111 which is oriented in the upstream direction and which faces the fixed abutment surface 110 oriented in the downstream direction.

The spring 106 is here mounted around an internal tubular guide portion 112 of the cylinder body 56.

The assistance device 50 comprises a cam mechanism 114 which is driven by the axial movement of the piston 32, and which forms a regulation means 115 for varying the value of the assistance force $F_a$ according to the travel $C_p$ of the pedal 22 in accordance with a predetermined assistance law.

The cam mechanism 114 comprises, for example, two moving rollers 116, 118 which each travel over an associated control surface 120, 122.

The two rollers 116, 118 are here arranged on each side of the piston 32 and are diametrically opposed.

The rotation axis A2 of each roller 116, 118 is substantially orthogonal to the sliding axis A1 of the piston 32.

Each roller 116, 118 is connected by a downstream link 124 to the connecting rod 70 and by an upstream link 126 to the cup 108.

It should be noted that the connecting rod 70 here constitutes a transmission member 71 which enables the assistance device 50 to transmit the assistance force $F_a$ to the assistance piston 32.

On the roller 116, 118 side, the links 124, 126 are mounted for pivoting about the rotation axis A2 of the roller 116, 118.

The downstream link 124 is mounted for pivoting on the free end of an associated transverse arm 128, 130 of the connection rod 70.

According to the embodiment depicted here, the cylinder body 56 forms an envelope 132 that is roughly cylindrical around the assistance device 50. The envelope 132 is stepped in diameter.

Advantageously, the control surface 120, 122 associated with each roller 116, 118 is produced on the internal wall of the envelope 132.

The control surfaces 120, 122 are here substantially symmetrical with respect to an axial plane (A1) and extend roughly in the same axial plane.

Each control surface 120, 122 comprises an upstream portion 134 inclined with respect to the sliding axis A1 and a downstream portion 136 roughly parallel to the sliding axis A1.

The upstream portion 134 has here a rounded profile convex towards the axis A1 and towards the upstream end.

According to an advantageous embodiment, the distance between the pivot axes of each upstream link 126, 128 is such that, in the upstream position of the associated moving roller 116, 118, the roller goes beyond, towards the upstream end, the point B1 on the control surface 120, 122 where the upstream link 126, 128 is perpendicular to the control surface 120, 122, so that the relaxing force of the assistance spring 106 biases the moving roller 116, 118 towards its upstream position.

In another advantageous embodiment, when the piston 32 is occupying its downstream declutching position, the axial distance between the abutment surface 111 of the cup 108 and the fixed abutment surface 110 is greater than the axial dimension of the spring 106 in the relaxed state, so that the spring 106 does not axially bias the piston 32 towards its downstream position.

Figure 8:
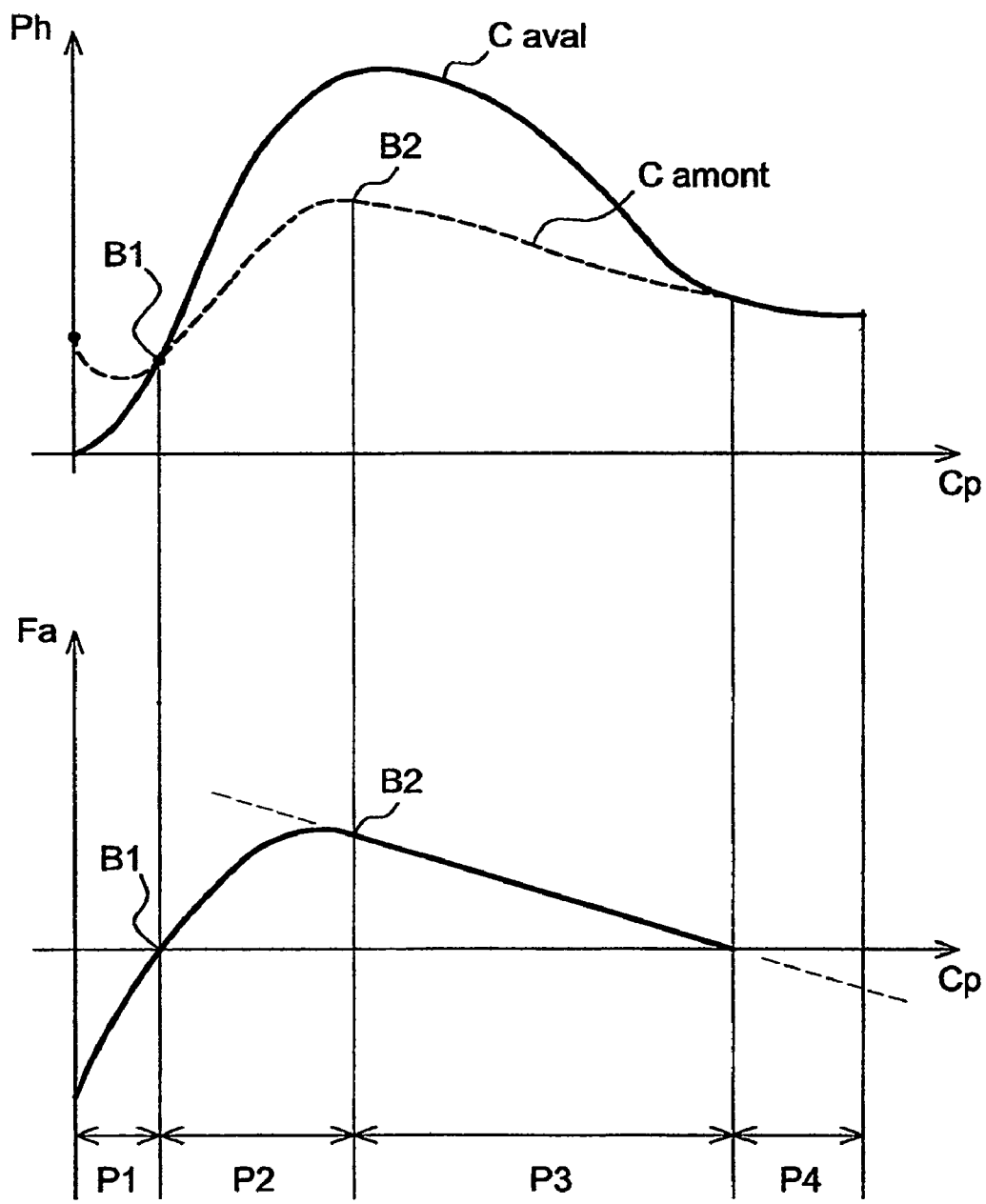
FIG. 8 is a diagram illustrating the change in hydraulic pressure in the control circuit and the change in the assistance force according to the travel of the clutch pedal.

The functioning of the cam mechanism 114 according to the invention is now explained, considering in particular the partial positions depicted in FIGS. 6 and 7 and the diagrams depicted in FIG. 8.

On the top part of FIG. 8, the curve $C_{aval}$ in continuous line represents a change in the hydraulic pressure $P_h$ in the downstream chamber of the assistance cylinder 30, during the declutching phase, as a function of the travel $C_p$ of the clutch pedal 22, and the curve $C_{amont}$ in a broken line represents the change in the hydraulic pressure $P_h$ in the upstream chamber of the assistance cylinder 30 during the declutching phase as a function of the travel $C_p$ of the clutch pedal 22.

In the bottom part of FIG. 8, the curve in a continuous line represents the change in the assistance force $F_a$ produced by the assistance spring 106, during the declutching phase, as a function of the travel $C_p$ of the clutch pedal 22, and the straight line in a broken line represents the stiffness of the assistance spring 106.

In the upstream position of the assistance piston 32, which is illustrated by the top part of FIG. 5, the spring 106 is compressed and axially biases (A1) each upstream link 126, as well as the associated roller 116, 118, towards the control surface 120, 122 and towards the outside, without causing any movement of the assistance piston 32.

The moving rollers 116, 118 are here held by the associated downstream link 124, which is connected to the assistance piston 32 in the upstream abutment position.

At the start of the declutching phase, the user presses on the control pedal 22 of the clutch 12 so as to move the piston of the sending cylinder 14 in the downstream direction.

The first part of the movement of the piston of the sending cylinder 14 corresponds to a dead travel, until the discharge orifice connecting the sending chamber 38 to the reservoir 29 closes.

Continuing its movement in the downstream direction, the piston of the sending cylinder 14 then causes an increase in the hydraulic pressure $P_h$ in the upstream chamber 34 of the assistance cylinder 30, which causes an axial movement A1 of the assistance piston 32 towards the downstream end.

The movement of the assistance piston 32 causes a movement of the rollers 116, 118 over the associated control surfaces 120, 122, towards the inside and towards the downstream direction.

During a first phase P1 of its axial movement, the assistance piston 32 causes an additional compression of the assistance spring 106, so that the assistance device 50 produces a resistance force which opposes the movement of the clutch pedal 22, which corresponds to a negative assistance force $F_a$, illustrated by the bottom part of FIG. 8.

During this first phase P1, the hydraulic pressure $P_h$ in the upstream chamber 34 of the assistance cylinder 30 is greater than the hydraulic pressure $P_h$ in the downstream chamber 36.

The first phase P1 of the movement of the piston 32 ends when the rollers 116, 118 reach the point B1 on the control surface 120, 122 where the upstream link 126, 128 is perpendicular to the control surface 120, 122, which is shown in FIG. 6.

At the moment when the rollers 116, 118 reach this point B1 of the control surface 120, 122, the relaxation force of the assistance spring 106 is cancelled by the reaction force of the control surface 120, 122, so that the hydraulic pressure $P_h$ equalises between the upstream chamber 34 and the downstream chamber 26 of the assistance cylinder 30.

It should be noted that, during the first phase P1, the axial movement of the piston 32 causes the closure of the connection 102 of the downstream chamber 36 with the reservoir 29, by virtue of the axial offset of the radial orifices 104 in the downstream direction.

During a second phase P2 of the axial movement of the assistance piston 32 in the downstream direction the assistance spring 106 commences to relax, producing an assistance force $F_a$ on the assistance piston 32.

The assistance force $F_a$ produced by the spring 106 is stepped down by the cam mechanism 114, according to the profile of the upstream portion 134 of the control surface 120, 122, which makes it possible to regulate the assistance force $F_a$ according to the travel $C_p$ of the pedal 22, in accordance with a predetermined assistance law.

The second phase P2 of the movement of the piston 32 ends when the rollers 116, 118 reach the downstream end B2 of the upstream portion 134 of the associated control surface 120, 122, as depicted in FIG. 7.

The assistance piston 32 then begins a third phase P3 of its axial movement, during which the rollers 116, 118 travel over the downstream portion 136 of the associated control surface, 120, 122.

During this third phase P3, the assistance spring 106 transmits all its relaxation force to the assistance piston 32 since the links 124, 126 are no longer pivoting and the rollers 116, 118 are no longer held axially by the control circuit 120, 122.

It should be noted that, during the third phase P3, the links 124, 126 can be close to an aligned position but it is preferable to keep a minimum inclination angle between the links 124, 126, as in FIG. 7 and on the bottom part of FIG. 5, so as to cause the links 124, 126 to pivot, during the return of the assistance piston 32 towards its upstream position, in order to prevent locking of the piston 32 in the cylinder 30.

According to the advantageous embodiment provided here, as the axial distance between the abutment surface 111 of the cup 108 and the fixed abutment surface 110 is greater than the axial dimension of the spring 106 in the relaxed state, the third phase P3 is followed by a fourth phase P4 during which the assistance piston 32 continues to slide as far as its downstream abutment position, without benefiting from an assistance force $F_a$ since the assistance spring 106 is in the relaxed state.

The fourth phase P4 is useful for minimising the friction forces caused by the assistance device 50 during the movement of the assistance piston 32, so as to guarantee the return of the piston 32 in the upstream direction, from its downstream position, in particular when the return force of the assistance piston 32 produced, for example, by the diaphragm 13 is small.

When the user releases his pressing on the pedal 22, the return elements of the clutch 12 such as the diaphragm 13 cause the return of the assistance piston 32 in the upstream direction.

The return of the piston 32 in the upstream direction causes a return of the cam mechanism 114 into its initial position and a compression of the assistance spring 106, which enables it to store elastic energy.

Preferably, at the end of the travel of the assistance piston 32 in the upstream direction, which corresponds to the first phase P1 of the movement of the piston 32 in the downstream direction, the assistance spring 106 causes an elastic return of the piston 32 as far as its upstream position, biasing the movable rollers 116, 118 towards their upstream idle positions.

In the upstream position of the piston 32, the orifices 104 of its downstream portion 66 come to be positioned opposite the radial groove 102, which connects the downstream hydraulic circuit 44 to the liquid reservoir 29.

Figure 9:
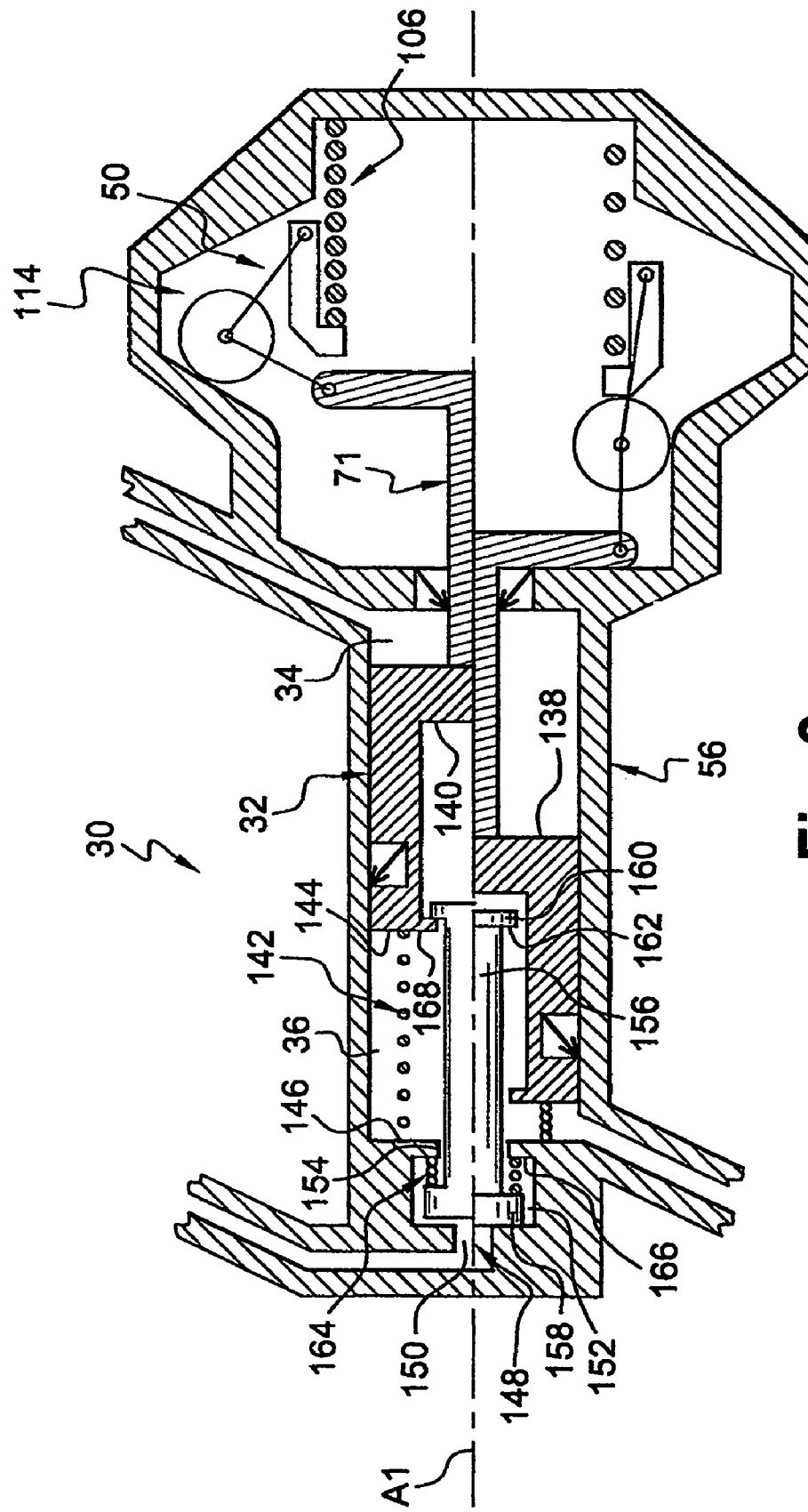
FIG. 9 is a view similar to that of FIG. 5 depicting schematically an assistance cylinder according to a second embodiment in which the assistance device is arranged at the upstream end of the assistance cylinder.

FIG. 9 depicts schematically a second embodiment of the control system 10 according to the invention.

It should be noted that the representation of the second embodiment has been simplified with respect to the representation of the first embodiment in FIG. 5.

This second embodiment is differentiated from the first mainly by the fact that the assistance device 50 is arranged at the upstream axial end of the assistance cylinder 30 rather than between the two hydraulic chambers 34, 36.

According to this embodiment, the assistance cylinder 30 comprises a piston 32 whose upstream transverse face 138 delimits the upstream chamber 34 and whose downstream transverse face 140 delimits the downstream chamber 36.

The piston 32 is here produced overall in a single piece.

According to the embodiment depicted here, a helical compression spring 142 is interposed axially between a downstream transverse end surface 144 of the piston 32 and the bottom wall 146 of the downstream chamber 36. This spring 142 serves to guarantee the return of the piston 32 as far as its upstream abutment position.

The assistance device 50 is produced in a similar manner to that of the first embodiment. It comprises in particular an assistance spring 106 and a cam mechanism 114.

The assistance device 50 comprises a transmission member 50 in the form of a transmission rod that extends axially towards the upstream transverse face 138 of the assistance piston 32.

According to an advantageous embodiment, depicted here, the transmission rod 71 cooperates solely by contact with the upstream transverse surface 138 of the assistance piston 32.

This configuration of the transmission rod 71 enables the assistance piston 32 to slide independently of the rod 71. Thus, where the pressure exerted by the assistance device 50 on the transmission rod 71 is less than the pressure exerted on the assistance piston 32 by the fluid contained in the upstream chamber 34, the assistance piston 32 can slide in the downstream direction without being slowed down by the movement of the assistance device 50.

Such a configuration also mitigates malfunctioning of the assistance device 50 since the control system 10 can function without assistance.

FIG. 9 also depicts a variant embodiment of the device for connecting the downstream chamber 36 to the reservoir 29.

Advantageously, the assistance cylinder 30 comprises here a discharge valve 148 which is controlled by the piston 32, so as to connect to the reservoir 29 when the piston 32 is occupying its upstream position.

To this end, the pipe connecting to the reservoir 29 emerges, through a discharge orifice 150, in an intermediate cylindrical cavity 152 which is arranged at the downstream axial end of the cylinder body 56.

The intermediate cavity 152 communicates with the downstream chamber 36 through an opening 154 that emerges in the bottom wall 146 of the downstream chamber 36.

The valve 148 comprises a rod or tail 156 which is provided, at its downstream axial end, with a head 158 able to close off the communication orifice 150, and at its upstream axial end with a control collar 160 delimiting a transverse abutment surface 162 oriented in the downstream direction.

The valve 148 is biased axially in the downstream direction and therefore towards the closure position of the discharge orifice 150, by a valve spring 164 interposed axially between the head 158 and a transverse annular rim 166, oriented in a downstream direction, of the intermediate cavity 152.

The control collar 160 of the valve 148 is designed to cooperate by contact with the upstream transverse surface of a transverse annular rim 168 arranged at the downstream axial end of the piston 32 so that, at the end of travel of the piston 32 in the upstream direction, the annular rim 168 comes into axial abutment against the transverse surface 162 of the control collar 160 in order to cause an axial movement of the valve 148 in the upstream direction, counter to its spring 164.

The movement of the valve 148 in the upstream direction causes the opening of the discharge orifice 150, which connects the downstream chamber 36 to the reservoir 29 at the end of the travel of the piston 32 in the upstream direction.

The functioning of the assistance cylinder 30 according to the second embodiment is similar to that of the assistance cylinder 30 according to the first embodiment.

Compared with the first embodiment, the discharge valve 148 according to the second embodiment has the advantage of requiring a shorter axial travel in order to cause the connection of the downstream chamber 36 to the reservoir 29, with a sufficient cross section of flow of the fluid.

Figure 10:
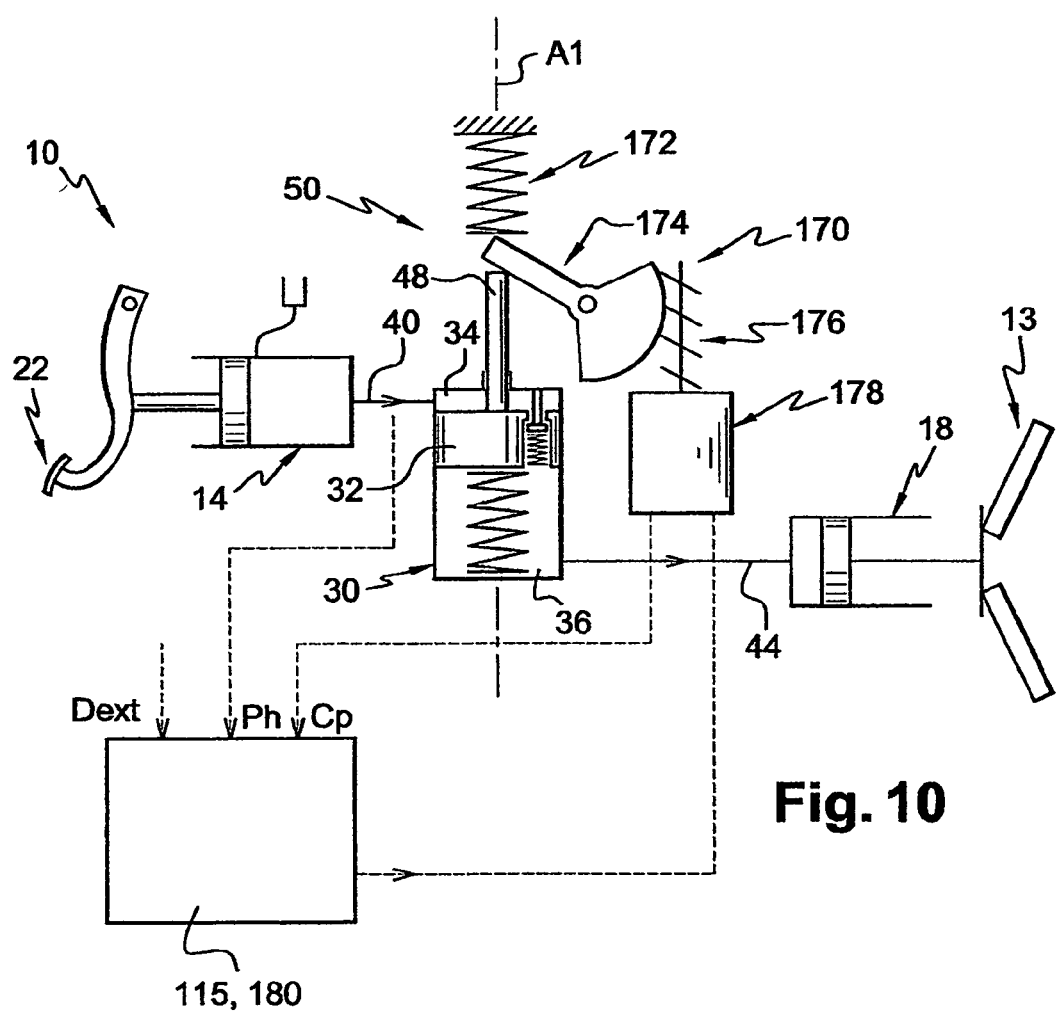
FIG. 10 is a diagram similar to that in FIG. 2 that depicts schematically a control system according to a third embodiment of the invention in which the relaxation of the assistance spring is controlled by an electrical actuator.

FIG. 10 depicts schematically a third embodiment of the control system 10 according to the invention, in which the assistance device 50 comprises an electrical actuator 170 that controls the relaxation of an elastic assistance element 172 during the declutching phase.

According to this embodiment, the assistance force $F_a$ is therefore produced by the relaxation of an elastic assistance element 172, here a helical compression spring, as in the first and second embodiments.

The cam mechanism 114 here has been replaced by the electrical actuator 170.

In the diagram in FIG. 10, the electrical actuator 170 comprises a lever 174 which is interposed axially between the rod 48 of the assistance piston 32 and the movable axial end of the assistance spring 172, and which is controlled pivotally by the transmission shaft 176 on the electric motor 178.

The assistance spring 172 stores elastic energy during the engagement phase, in particular under the effect of the elastic return of the clutch 12 towards its engagement position, which pushes the assistance piston 32 towards its upstream position.

During the declutching phase, the electrical actuator 170 releases the assistance spring 172 so as to produce the assistance force $F_a$ on the piston 32.

The motor 178 is preferably controlled by an electronic control unit 180 which constitutes a means 115 of regulating the assistance force $F_a$.

The control unit 180 controls, for example, the electric motor 178 in accordance with operating parameters such as:
the hydraulic pressure $P_h$ in the upstream circuit 40,
the travel $C_p$ of the clutch pedal 22,
data $D_{ext}$ external to the control system 10, for example data relating to the functioning of the vehicle engine, the functioning of the vehicle gearbox, the functioning of the clutch 12, etc.

The operating parameters can be supplied to the control unit 180 by sensors (not shown).

The value of the travel $C_p$ of the pedal 22 can be supplied to the control unit 189 by the electric motor 178, in particular in the case where the rotation of its transmission shaft is linked to the sliding of the assistance piston 32.

The control unit 180 can modulate the assistance force $F_a$ according to at least one predetermined assistance law.

A fourth and fifth embodiment of the control system 10 according to the invention are now described, in which the assistance device 50 is connected to an energy source 182, 184 which is external to the control system 10 and which is installed in the vehicle that the control system 10 equips.

According to these embodiments, the assistance force $F_a$ is produced by the external energy source 182, 184 and is then transmitted to the assistance piston 32.

Figure 11:
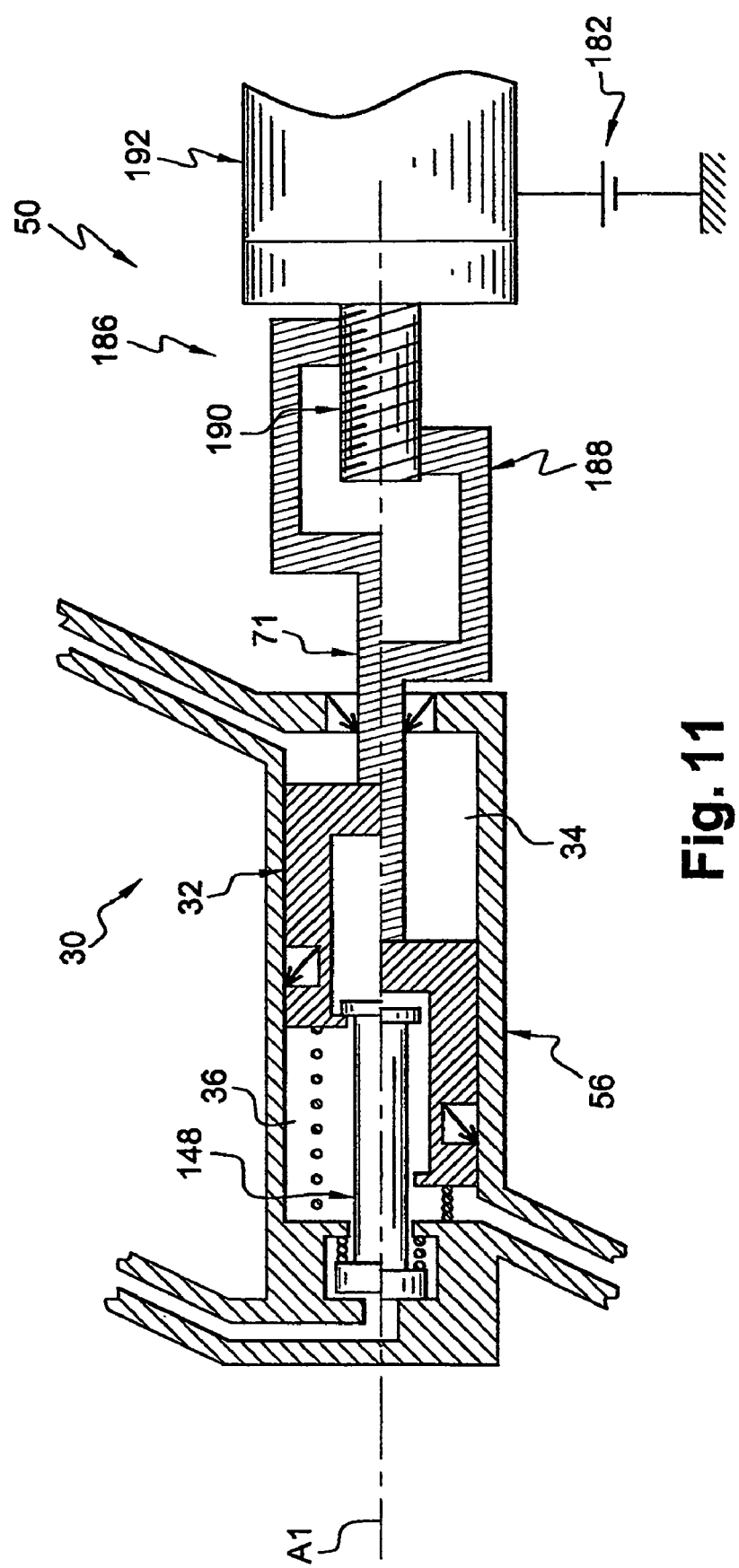
FIG. 11 is a diagram similar to that of FIG. 9 that depicts an assistance cylinder according to a fourth embodiment of the control system according to the invention in which the assistance force is produced by an electric motor.

In the fourth embodiment, depicted in FIG. 11, the external energy source 182 consists of a source of electric current, which may be the system supplying electrical energy to the vehicle.

The assistance cylinder 30 of the fourth embodiment is roughly similar to that of the second embodiment, depicted in FIG. 9, except that the cam mechanism 114 of the assistance device 50 is replaced by an electrical actuator 186 which acts directly on the transmission rod 71.

According to the embodiment depicted, the transmission rod 71 is equipped, at its upstream axial end, with a threaded portion 188 which is mounted screwed on a threaded shaft 190 able to be driven in rotation about its axis A1 by an electric motor 192, which is connected to the source of electric current 182.

Advantageously, the electric motor 154 can be controlled by an electronic control unit (not shown in FIG. 11) in the same way as the third embodiment described above (FIG. 10).

In the fifth embodiment, illustrated by FIGS. 12 to 19, the external energy source 184 consists of a hydraulic or pneumatic pressure source.

In the remainder of the description, non-limitingly, solely a hydraulic pressure source 184 will be considered, although a pneumatic pressure source can also be envisaged.

Figure 12:
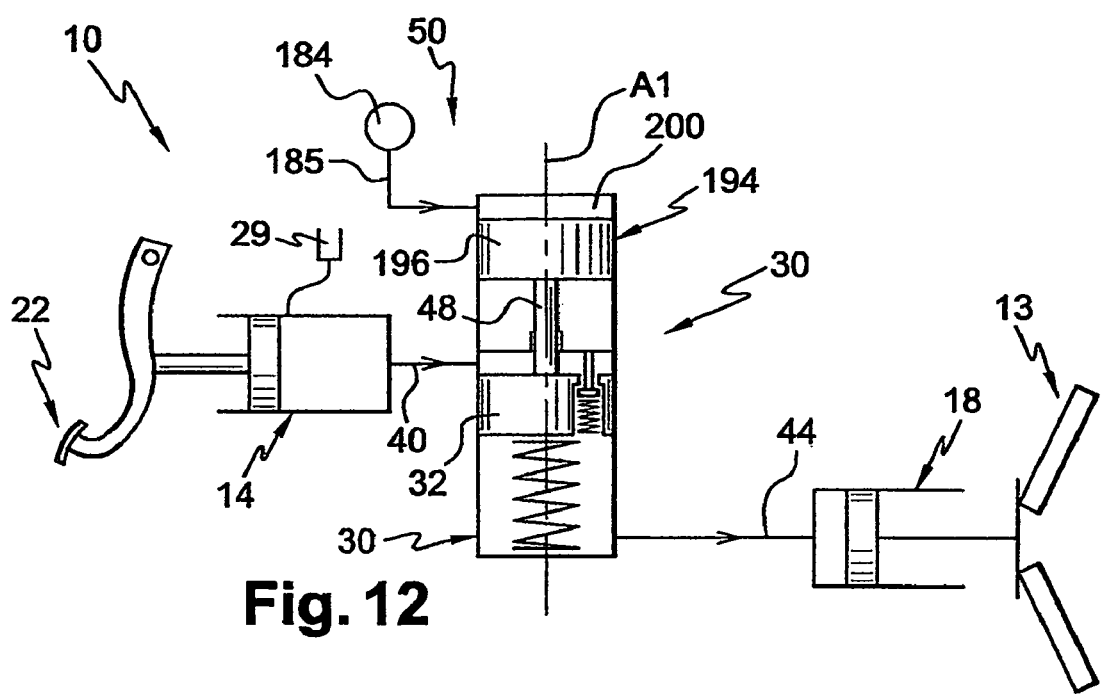
FIG. 12 is a diagram similar to that of FIG. 2 that depicts schematically a control system according to a fifth embodiment of the invention in which the assistance force is produced by a ram connected to a pressure source.

FIG. 12 illustrates the operating principle of the fifth embodiment.

In the fifth embodiment, the control rod 48 of the assistance piston 32 is linked in axial movement (A1) to a ram 194 connected to the pressure source 184 by an auxiliary control circuit 185, so as to transmit an assistance force $F_a$ to the assistance piston 32 during the declutching phase.

The ram 194 comprises a so-called auxiliary piston 196 which slides in an auxiliary cylinder 198 and which, upstream, delimits an auxiliary control chamber 200.

The auxiliary piston 194 cooperates, for example, by contact with the control rod 48 of the assistance piston 32.

During the declutching phase, the pressure source 184 causes an increase in the hydraulic pressure $P_h$ in the control chamber 200 of the ram 194, which produces an assistance force $F_a$ on the assistance piston 32, by means of the control rod 48, or transmission rod.

Figure 13:
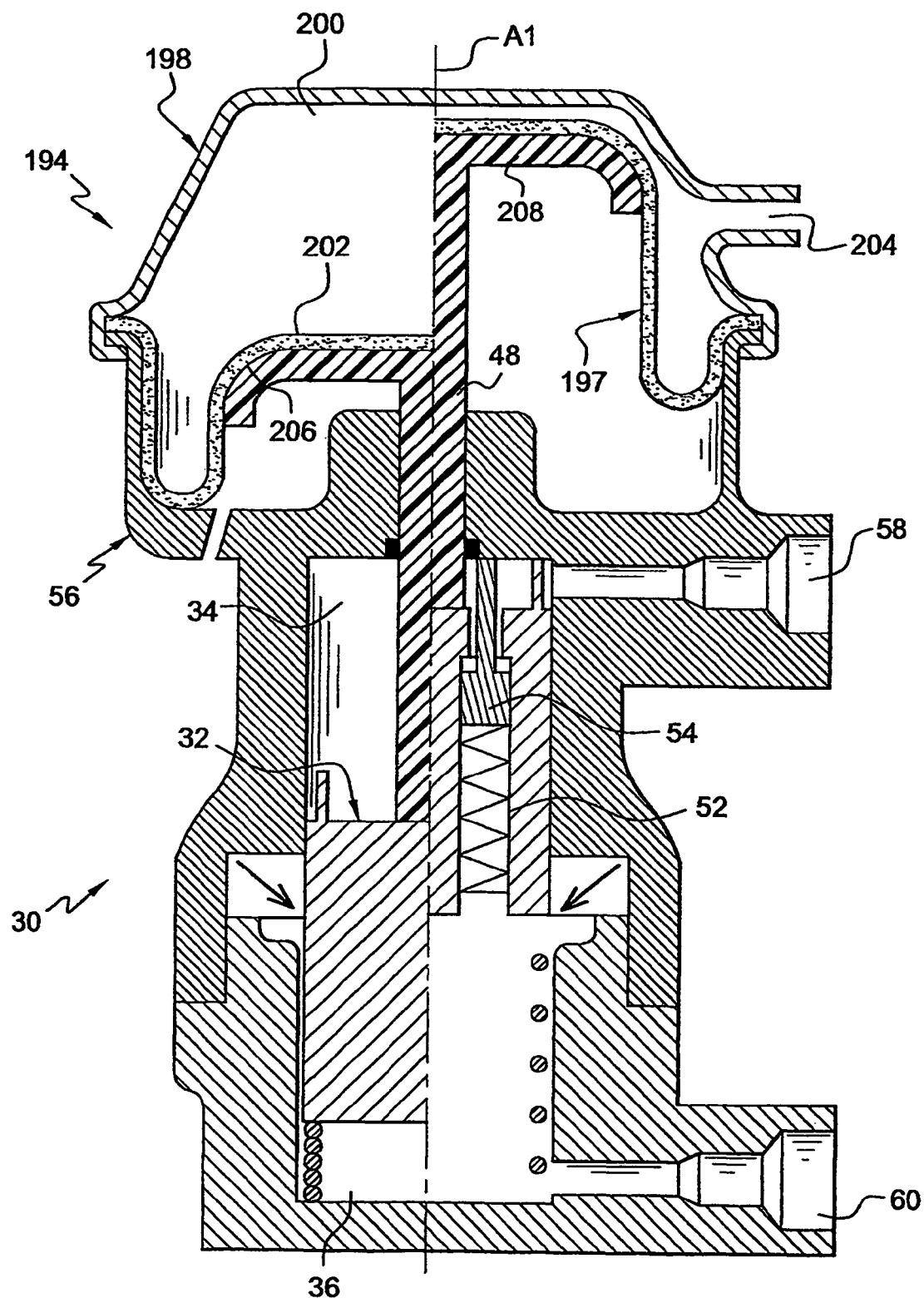
FIG. 13 is a view in axial section that depicts an assistance cylinder adapted to the control system of FIG. 12 and comprising a membrane ram.

FIG. 13 depicts an example of an assistance cylinder 30 equipped with a ram 194 in accordance with the teachings of the invention, and in which the auxiliary piston 196 is replaced by a flexible membrane 197, or "unwinding" membrane.

On the left-hand part of FIG. 13, the assistance piston 32 is shown in the downstream position and on the right-hand part the assistance piston 32 is shown in the upstream position.

The assistance piston 32 is here produced in a similar manner to that of the second embodiment (FIG. 9), except that the discharge orifice 52 and the discharge valve 54 are produced in an axial orientation in the body of the assistance piston 32, as on the variant described with reference to FIG. 4.

The discharge orifice 52 is offset with respect to the axis to allow a centred abutment of the rod 48 on the piston 32. In the case of an inclined mounting of the assistance cylinder 30, the orifice 52 is put in the high position in order to guarantee the purging of the air downstream of the piston 32, at the time of mounting.

The auxiliary cylinder 198 of the ram 194 is arranged here at the upstream axial end of the assistance cylinder 30. The auxiliary cylinder 198 can be formed in an extension of the assistance cylinder body 56.

The membrane 197 is sealed in the auxiliary cylinder so as to delimit, on the same side as its upstream transverse face 202, the control chamber 200 which is connected to the pressure source 184 by an auxiliary orifice 204.

The membrane 197 is here of the single-acting type since its downstream transverse face 206 is exposed to atmospheric pressure.

The control rod 48 of the assistance piston 32, or transmission road, comprises at its upstream axial end an abutment disc 208 which is in contact with the downstream transverse face 206 of the membrane 197.

When the hydraulic pressure $P_h$ increases in the control chamber 200, exceeding atmospheric pressure, the membrane 197 "unwinds", exerting an axial abutment force directed in the downstream direction on the disc 208, which produces an assistance force $F_a$ on the piston 32, by means of the transmission rod 48.

Figure 19:
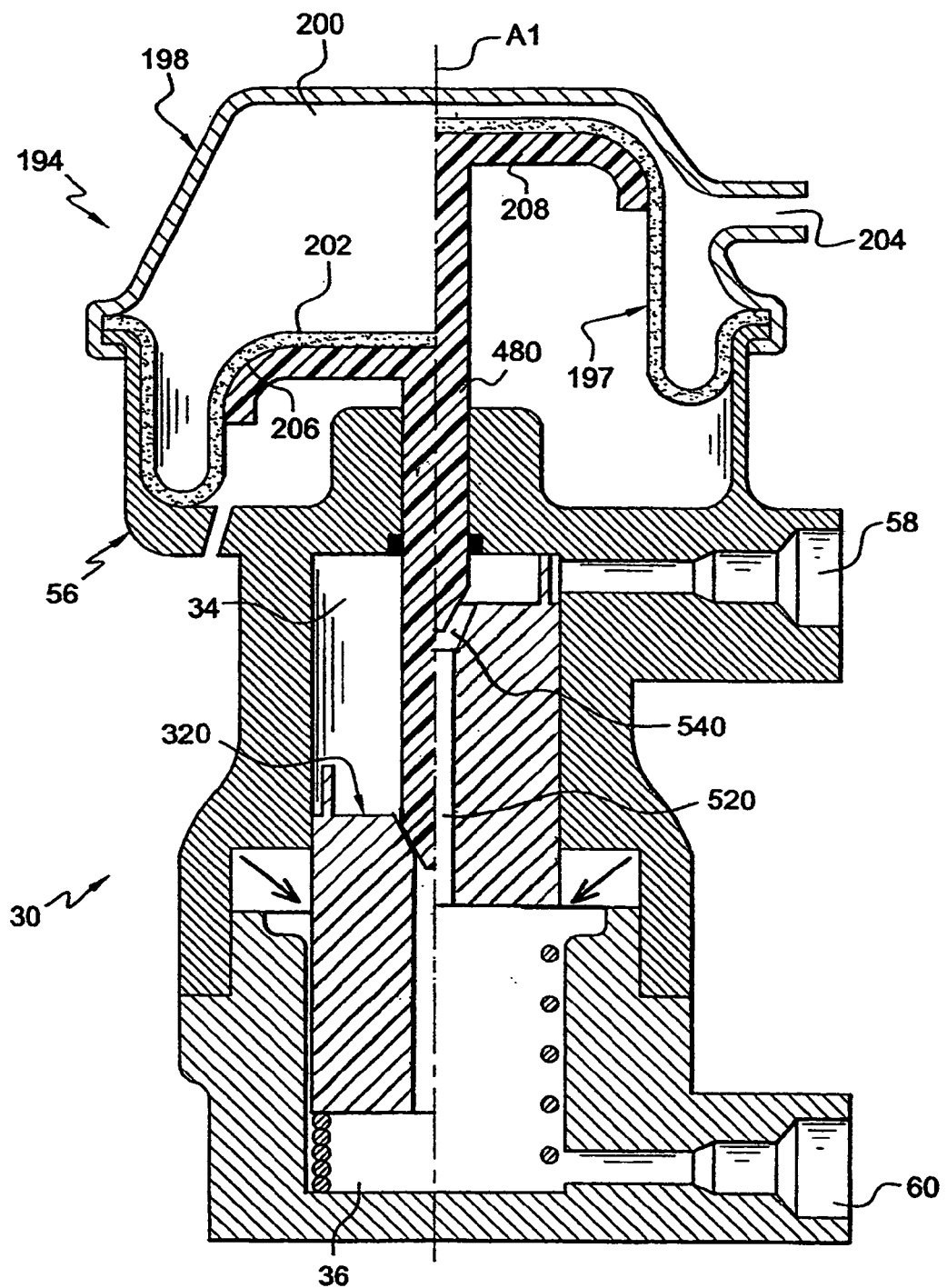
FIG. 19 is a view in axial section depicting a variant of the embodiment in FIG. 13.

A variant of this latter embodiment, illustrated in FIG. 19, consists of using the abutment between the rod 480 on the piston 320 in order to control the opening of a discharge orifice 520. In this case, the orifice 520 is a channel pierced in the piston 320 along the axis of the rod 480, and the end of this rod 480 has a complementary shape with respect to that of the outlet 540 of the orifice 420 so as to achieve the obstruction of this orifice when the rod is in abutment on the piston. An elastomer seal can be placed between the rod and the piston.

When the clutch is engaged and the assistance is not activated, a small clearance is created between this rod 480 and the piston 320, the orifice 520 is free. This orifice closes when the assistance force occurs. This variant is simple to implement since it does not require any supplementary part and keeps all the advantages of the discharge orifices presented above.

FIGS. 14 to 18 illustrate several possible solutions for regulating the assistance force $F_a$ produced by the ram 194.

Figure 14:
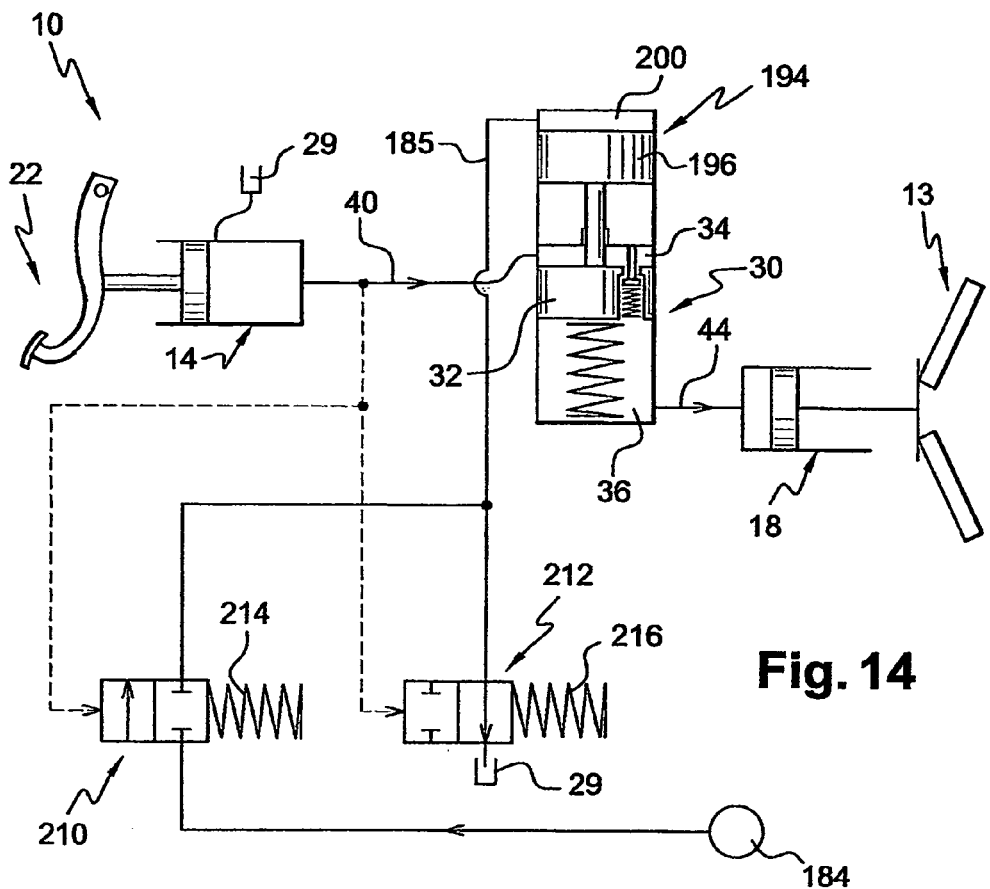
FIGS. 14, 16 and 18 are diagrams similar to that in FIG. 2 that illustrate three different solutions for regulating the assistance force adapted to the control system of FIG. 12.
Figure 15:
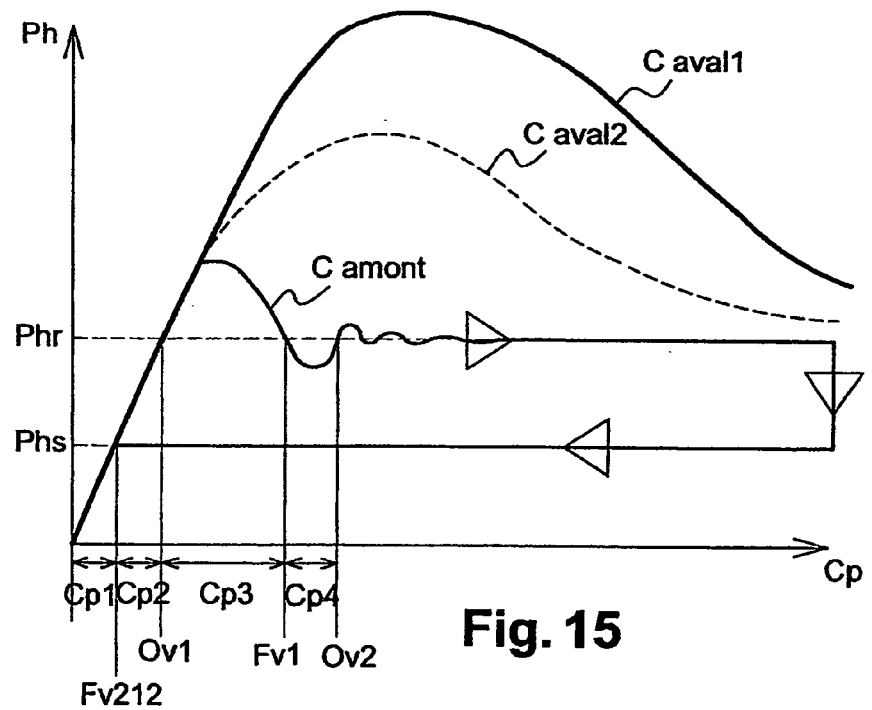
FIGS. 15 and 17 are diagrams illustrating the assistance laws associated respectively with the first two solutions depicted in FIGS. 14 and 16.

According to a first solution, illustrated by FIGS. 14 and 15, the means 115 of regulating the assistance force $F_a$ consists of two control valves 210, 212 which constitute respectively a charging valve 210 and a discharge valve 212 and which are connected by the auxiliary circuit 185 to the control chamber 200 of the ram 194.

In addition, the charging valve 210 is connected to the pressure source 184 and the discharge valve is connected to a fluid reservoir 29.

A charging valve 210 and a discharge valve 212 are controlled here by the hydraulic pressure $P_h$ in the upstream circuit 40 counter to the return force of a spring 214, 216 associated with each valve 210, 212.

Advantageously, the stiffness of the spring 214 associated with the charging valve 210 is greater than the stiffness of the spring 216 associated with the discharge valve 212, so that the opening of the charging valve 210 and the closing of the discharge valve 212 are offset in time, during the declutching travel.

In FIG. 14, the control system 10 is depicted at rest, in the engaged position, which corresponds to an absence of pressure in the upstream hydraulic circuit 40.

In this position, the charging valve 210 is closed and the discharge valve 212 is open, so that the auxiliary circuit 185 is connected to the reservoir 29.

An explanation is now given of the functioning of the control system 10 of the FIG. 14, during the declutching phase, considering in particular FIG. 15.

In FIG. 15, the curve $C_{aval1}$ in a continuous line represents the change in the hydraulic pressure $P_h$ in the downstream chamber 36 of the assistance cylinder 30 during the declutching phase, as a function of the travel $C_p$ of the clutch pedal 22, when the clutch 12 is worn.

The curve $C_{aval2}$, in a broken line, represents the same change as the curve $C_{aval1}$, when the clutch 12 is new.

When the clutch 12 wears, the hydraulic pressure $P_h$ necessary for performing the declutching operation increases.

The curve $C_{amont}$ in a continuous line represents the change in the hydraulic pressure $P_h$ in the upstream chamber 34 of the assistance cylinder 30, during the declutching phase, as a function of the travel $C_p$ of the clutch pedal 22.

When the clutch pedal 22 is actuated, the hydraulic pressure $P_h$ in the upstream circuit 40 increases.

After a first travel $C_{p1}$ of the pedal 22, the hydraulic pressure $P_h$ reaches a first threshold value $P_{hs}$ which is sufficient to cause the movement of the discharge valve 212 counter to its spring 216, which causes the closure $F_{v212}$ of the discharge valve 212.

After a second travel $C_{p2}$ of the pedal 22, the hydraulic pressure $P_h$ reaches a second threshold value $P_{hr}$, referred to as the regulated value, which is sufficient to cause the movement of the charging valve 210 counter to its spring 214, which causes the first opening $O_{v1}$ of the charging valve 210.

The charging valve 210 being open, the pressure source 184 is connected to the control chamber 200 of the ram 194, which produces an assistance force $F_a$ on the piston 32.

The assistance force $F_a$ applied to the piston 32 causes a reduction in the hydraulic pressure $P_h$ in the upstream circuit 40 so that, after a given lapse of time, which corresponds to a third travel $C_{p3}$ of the pedal 22, the charging valve 210 returns to its idle position, which corresponds to a first closure $F_{v1}$ of the charging valve 210.

It should be noted that the discharge valve 212 remains closed since the hydraulic pressure $P_h$ in the upstream circuit 40 does not drop as far as the threshold value $P_{hs}$ associated with this valve 212.

The return of the charging valve 210 to its idle position once again causes an increase in the hydraulic pressure $P_h$ in the upstream circuit 40 since, the pedal 22 continuing its pressing-down travel, there is a drop in pressure in the control chamber 200 due to the descent of the ram 196.

After a fourth travel $C_{p4}$ of the pedal 22, the hydraulic pressure $P_h$ once again reaches the regulated value, which causes a second opening $O_{v2}$ of the charging valve 210.

This succession of openings and closings of the charging valve 210 continues until the assistance piston 32 is occupying its downstream position.

In practice, in order to limit these oscillations, use is made of a charging valve 210 which opens and closes progressively for small oscillations from the regulated value $P_{hr}$; in this way, the openings and closings are not abrupt and the equilibrium position is reached more rapidly.

The charging valve 210 therefore allows a closed-loop regulation of the hydraulic pressure $P_h$ in the upstream chamber 34 of the assistance cylinder 30, which stabilises around the regulated value $P_{hr}$.

Consequently, as the hydraulic pressure $P_h$ in the upstream chamber 34 of the assistance cylinder 30 is linked to the pressure $P_h$ in the sending cylinder 14, the force that the user must apply to the pedal 22 tends towards a constant value throughout the declutching phase.

When the user releases the pedal 22, the hydraulic pressure $P_h$ decreases in the upstream chamber 34, which first of all causes the closure of the charging valve 210 and then, having arrived at the first threshold value $P_{hs}$, the opening of the discharge valve 212 permitting the return of the assistance piston 32 to its upstream position.

One advantage of this solution is that the force used by the user on the pedal 22 is not dependent on the wear on the clutch 12.

This advantage is illustrated in FIG. 15 by the fact that the pressure curve $C_{amont}$ is identical for the two pressure curves $C_{aval1}$, $C_{aval2}$ associated with the downstream chamber 36, the one corresponding to a worn clutch 12 and the one corresponding to a new clutch 12.

Figure 16:
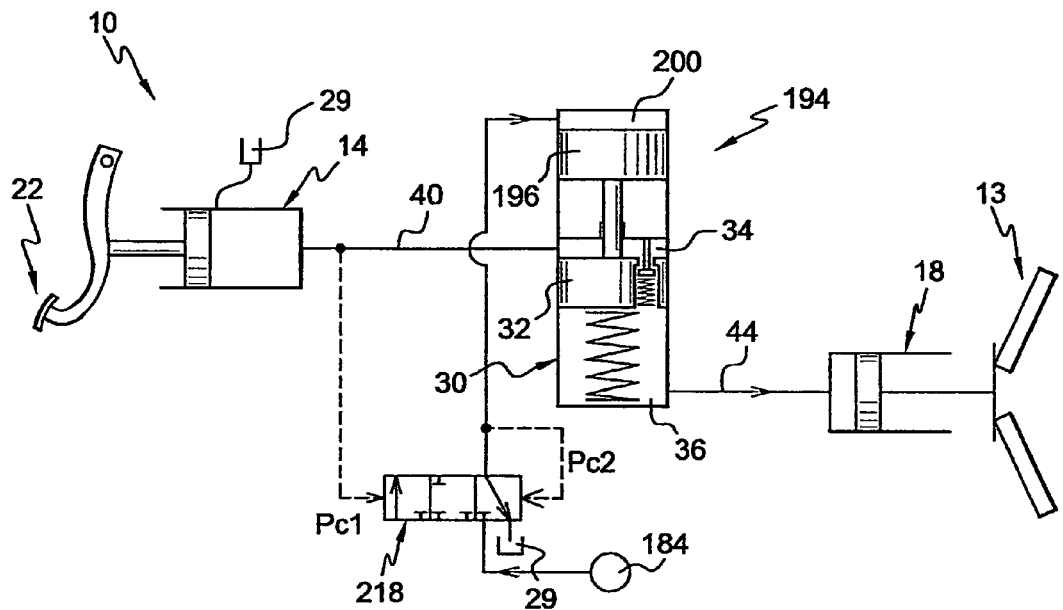
Figure 17:
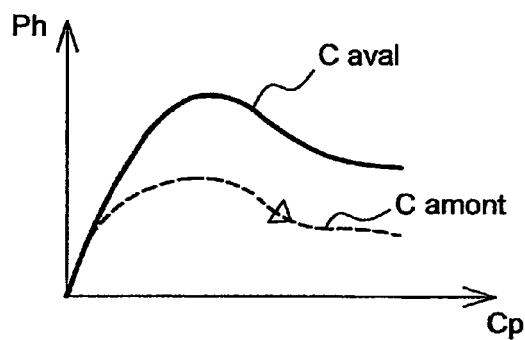

According to a second solution, which is illustrated by FIGS. 16 and 17, the two valves 210, 212 provided in the first solution are replaced by a single three-position control valve 218.

A first position of the control valve 218, referred to as the charging position, causes the connection of the control chamber 200 to the pressure source 184.

A second position, or intermediate position, of the control valve 218 corresponds to a closure position of the control valve 218.

A third position of the control valve 218, referred to as the discharge position, causes the connection of the control chamber 200 to the fluid reservoir 29.

In FIG. 16, the control valve 218 is shown in its discharge position.

The control valve 218 has two control pressures $P_{c1}$, $P_{c2}$ which are applied on each side of the control valve 218 with identical abutment surfaces.

The first control pressure $P_{c1}$ corresponds to the hydraulic pressure $P_h$ in the upstream chamber 34 of the assistance cylinder 30, and is applied at the same side as the first position.

The second control pressure $P_{c2}$ corresponds to the hydraulic pressure $P_h$ in the control chamber 200 of the ram 194 and is applied at the third position.

The functioning of the control valve 218 is as follows.

When the two control pressures $P_{c1}$, $P_{c2}$, are equal, that is to say when the hydraulic pressure $P_h$ is equal in the upstream chamber 34 and in the control chamber 200, the control valve 218 occupies its intermediate closure position.

When the first control pressure $P_{c1}$ is greater than the second control pressure $P_{c2}$, that is to say when the pressure in the upstream chamber 34 is greater than the pressure in the control chamber 200, the control valve 218 occupies its charging position.

When the first control pressure $P_{c1}$ is less than the second control pressure $P_{c2}$, that is to say when the pressure in the upstream chamber 34 is less than the pressure in the control chamber 200, the control valve 218 occupies its discharge position.

The embodiment depicted in FIG. 16 thus makes it possible to effect a so-called proportional regulation of the assistance force $F_a$, which is illustrated by FIG. 17.

The curve $C_{aval}$ in a continuous line represents the change in the hydraulic pressure $P_h$ in the downstream chamber 36 of the assistance cylinder 30, during the declutching phase, as a function of the travel $C_p$ of the clutch pedal 22.

The curve $C_{amont}$ in a broken line represents the change in the hydraulic pressure $P_h$ in the upstream chamber 34 of the assistance cylinder 30, during the declutching phase, as a function of the travel $C_p$ of the clutch pedal 22.

It is found that, in the particular case, illustrated here, where the abutment surfaces of the control pressures $P_{c1}$, $P_{c2}$ are identical, the assistance force $F_a$ produces approximately one half of the total force to be supplied on the piston of the receiving cylinder 18.

Naturally, it is possible to modify the ratio between the assistance force $F_a$ and the total source to be supplied by modifying the ratio between the abutment surfaces of the control pressures $P_{c1}$, $P_{c2}$.

Figure 18:
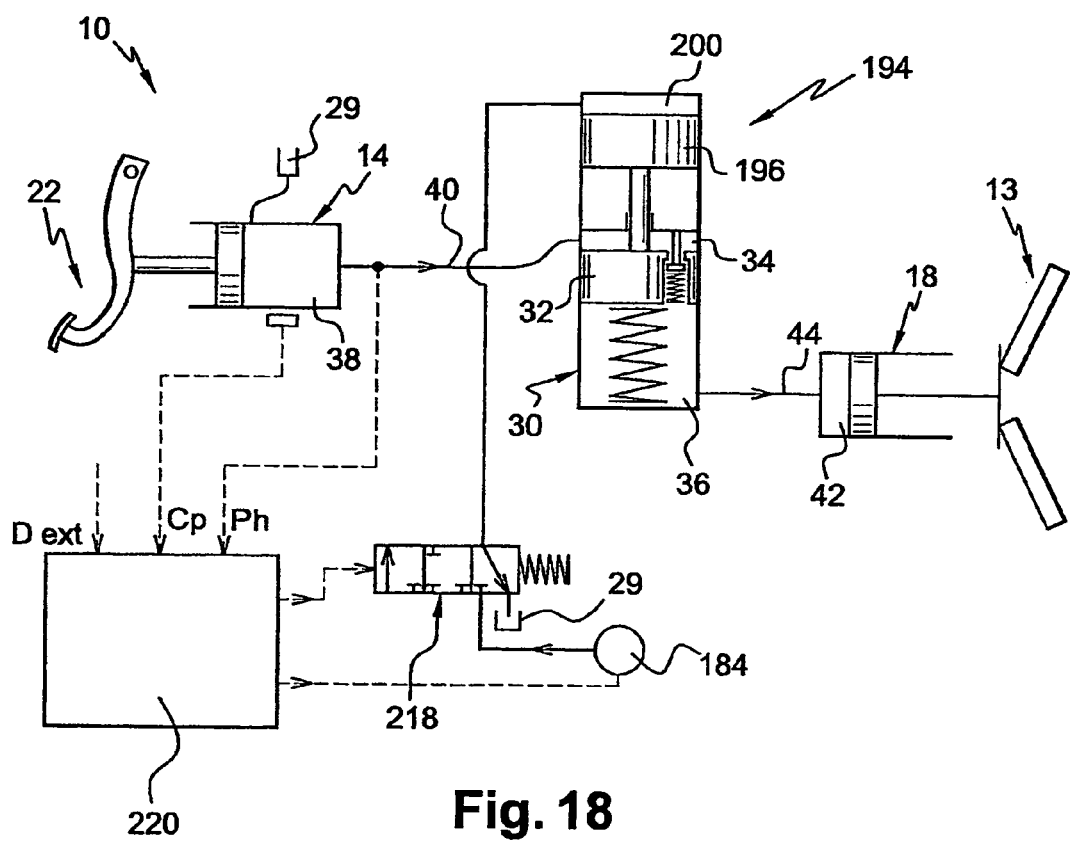

FIG. 18 depicts a third solution in which the regulation means 115 is a three-position control valve 218, as in FIG. 18, but which is differentiated from the second solution in that the control valve 218 is controlled by an electronic control unit 220.

The control unit 220 can control the control valve 218 according to control parameters measured by sensors such as the travel of the pedal $C_p$, the hydraulic pressure in the upstream chamber 34 and external data $D_{ext}$.

The control unit 220 can also control the pressure source 184, which makes it possible to precisely apportion the required assistance force $F_a$.

According to the embodiment depicted in FIG. 18, by virtue of the control unit 220, it is possible to precisely choose the required assistance curve. In particular, it is possible to reproduce the assistance curve of the first and second solutions (FIGS. 15 and 17).

It should be noted that the embodiments of the control system 10 according to the invention, which are depicted with the discharge valve 54 produced axially in the assistance piston 32 and with a single connection to the fluid reservoir 29, could have been represented with two connections of the reservoir 29, as depicted and described in particular with reference to FIGS. 2 and 3.

According to a variant (not shown) of the various embodiments described above, it is possible to add in the fluid passage, either in the upstream 40 or downstream 44 circuit, or in the control circuit 185 of the assistance ram 196, a device reducing the cross section of flow of the fluid in the direction of engagement.

This device can be a valve that occupies a first position forming a maximum cross section of flow in the direction of disengagement, and a second position forming a reduced cross section of flow in the direction of engagement.

Such a device makes it possible in particular to avoid an impact when releasing the pedal 22 too rapidly.

More generally, the assistance device 5 can comprise a regulation means 218 which varies the value of the assistance force $F_a$ as a function of the upstream pressure $P_h$ in the upstream chamber 34 of the assistance cylinder 30, or the downstream pressure $P_h$ in the downstream chamber 36, or a combination of the two pressures, according to a predetermined assistance law.

The invention claimed is:

1. A hydraulic control system (10) for a clutch (12) for a motor vehicle, comprising:
   an upstream sending cylinder (14) connected by a conduit (16) to a downstream receiving cylinder (18), so as to form a hydraulic control circuit (19);
   an assistance cylinder (30) interposed in the conduit (16), between the upstream sending cylinder (14) and the downstream receiving cylinder (18); and
   at least one assistance piston (32) mounted so as to slide axially along a sliding axis (A1) in a body (56) of the assistance cylinder (30) between an upstream engagement position and a downstream disengagement position, so as to delimit an upstream hydraulic chamber (34) and a downstream hydraulic chamber (36) with variable volumes according to the axial position of the assistance piston (32);
   the upstream chamber (34) being connected to the upstream sending cylinder (14) by a portion of hydraulic circuit referred to as an upstream circuit (40) and the downstream hydraulic chamber (36) being connected to the downstream receiving cylinder (18) by a portion of the hydraulic circuit referred to as a downstream circuit (44);
   each hydraulic circuit portion (40, 44) comprising a means (52, 102, 150) of relevelling the volume of fluid connected to at least one fluid reservoir (29);
   the assistance cylinder (30) comprising an assistance device (50) applying an assistance force (Fa) to the assistance piston (32) during a disengagement phase of the clutch (12);

the assistance device (50) comprising a regulation means (114, 115) varying the value of the assistance force (Fa) according to the travel (CP) of a clutch control pedal (22) in accordance with a predetermined assistance law;

the assistance device (50) further comprising an elastic element (106) storing energy during an engagement phase of the clutch (12) and restoring the energy during the disengagement phase in order to produce the assistance force (Fa);

the elastic element (106) compressed when the assistance piston (32) being in the upstream engagement position and expanded when the assistance piston (32) being in the downstream disengagement position;

the regulation means (115) being a cam mechanism (114) driven by the axial movement of the piston (32) for regulating the assistance force ($F_a$) produced by the elastic element (106) during the disengagement phase.

2. The control system (10) according to claim 1, wherein the assistance device (50) comprises a transmission member (48, 70, 71) which transmits the assistance force (Fa) to the assistance piston (32).

3. The control system (10) according to claim 2, wherein the transmission member (48, 70, 71) is connected in terms of axial movement to the assistance piston (32) in both directions of sliding of the piston (32).

4. The control system (10) according to claim 2, wherein the transmission member (48, 71) cooperates by contact with an associated abutment surface (138) of the assistance piston (32) so that, in the case where the speed of the assistance device (50) is less than the speed of the assistance piston (32), the assistance device (50) does not slow down the sliding of the assistance piston (32) towards the downstream end.

5. The control system (10) according to claim 2, wherein the transmission member (48, 71) is arranged at an axial end of the assistance piston (32).

6. The control system (10) according to claim 2, wherein the piston (32) comprises an upstream portion (62) that delimits the upstream chamber (34) and a downstream portion (66) that delimits the downstream chamber (36), and the two portions (62, 66) are connected in axial movement by a connecting rod (70), and in that the connecting rod (70) constitutes the transmission member (71) of the assistance device (50).

7. The control system (10) according to claim 2, wherein the hydraulic circuit (19) is connected to a fluid reservoir (29) in the engagement position; and wherein the assistance cylinder (30) comprises at least one discharge orifice (52, 102, 150) formed in the body (56) thereof, which makes the downstream hydraulic chamber (36) communicate with the fluid reservoir (29), when the assistance piston (32) is occupying its upstream position, so as to compensate for the variations in hydraulic volume in the hydraulic circuit (19) over time.

8. The control system (10) according to claim 7, wherein the discharge orifice (52, 150) comprises a valve (54, 148) that is controlled by the axial movement of the assistance piston (32).

9. The control system (10) according to claim 1, wherein the assistance device (50) is housed in the cylinder body (56); and wherein the cam mechanism (114) comprises at least one control surface (120, 122) that is produced on an internal wall of the cylinder body (56).

10. The control system (10) according claim 9, wherein the elastic assistance element (106) is an axial compression elastic element that is interposed axially between a cup (108) and an abutment surface (110) fixed with respect to the assistance cylinder body (56), wherein the cam mechanism (114) comprises at least one movable roller (116, 118) which travels over the control surface (120, 122) between an upstream position and a downstream position corresponding respectively to the upstream and downstream positions of the assistance piston (32), and wherein the movable roller (116, 118) is connected by a first connecting rod (124) to the piston (32) and by a second connecting rod (126) to the cup (108).

11. The control system (10) according to claim 10, wherein the axis by which the connecting rods (124, 126) pivot on the movable roller (116, 118) is concurrent with the rotation axis (A2) of the roller (116, 118).

12. The control system (10) according to claim 11, wherein the control surface (120, 122) comprises an upstream portion (134) inclined with respect to the sliding axis (A1), and a downstream portion (136) substantially parallel to the sliding axis (A1) so that, during a first part of the disengagement phase, the movable roller (116, 118) moves first of all on the inclined portion (134) towards the axis (A1) and in the downstream direction, from the upstream position thereof, transmitting part of the relaxation force of the elastic assistance element (106) to the assistance piston (32), by a step-down effect, and then, during a second part of the disengagement phase, the movable roller (116, 118) moves on the downstream portion (136) in the downstream direction, in a substantially axial direction, transmitting all the relaxation force of the elastic assistance element (106) to the assistance piston (32).

13. The control system (10) according to claim 12, wherein the distance between the pivot axes of the second connecting rod (126) is such that, in the upstream position of the movable roller (116, 118), the roller moves in the upstream direction beyond a point (B1) on the control surface (120, 122) where the second connecting rod (126) is perpendicular to the control surface (120, 122), so that the expansion force of the elastic assistance element (106) biases the movement roller (116, 118) towards its upstream position.

14. The control system according to claim 1, wherein the regulation means (218) varies the value of the assistance force (Fa) according to the upstream pressure in the upstream chamber (34) of the assistance cylinder (30) or the downstream pressure in the downstream chamber (36), or a combination of the two pressures according to the predetermined assistance law.

15. The control system (10) according to claim 1, further comprising at a return spring (142) disposed in the downstream hydraulic chamber (36) for biasing the piston (32) towards the upstream position thereof.

16. A hydraulic control system (10) for a clutch (12) for a motor vehicle comprising:

an upstream sending cylinder (14) connected by a conduit (16) to a downstream receiving cylinder (18), so as to form a hydraulic control circuit (19);

an assistance cylinder (30) interposed in the conduit (16), between the upstream sending cylinder (14) and the downstream receiving cylinder (18); and at least one assistance piston (32) mounted so as to slide axially along a sliding axis (A1) in a body (56) of the assistance cylinder (30) between an upstream engagement position and a downstream disengagement position, so as to delimit an upstream hydraulic chamber (34) and a downstream hydraulic chamber (36) with variable volumes according to the axial position of the assistance piston (32);

the upstream chamber (34) being connected to the upstream sending cylinder (14) by a portion of hydraulic circuit referred to as an upstream circuit (40) and the downstream hydraulic chamber (36) being connected to the downstream receiving cylinder (18) by a portion of the hydraulic circuit referred to as a downstream circuit (44);

each hydraulic circuit portion (40, 44) comprising a means (52, 102, 150) of relevelling the volume of fluid connected to at least one fluid reservoir (29);

the assistance cylinder (30) comprising an assistance device (50) disposed in the cylinder body (56) for applying an assistance force (Fa) to the assistance piston (32) during a disengagement phase of the clutch (12);

the assistance device (50) comprising a regulation means (114, 115) varying the value of the assistance force (Fa) according to the travel (CP) of a clutch control pedal (22) in accordance with a predetermined assistance law, and an elastic element (106) for storing energy during an engagement phase of the clutch (12) and for restoring the energy during the disengagement phase in order to produce the assistance force (Fa);

the regulation means (115) being a cam mechanism (114) driven by the axial movement of the piston (32) for regulating the assistance force ($F_a$) produced by the elastic assistance element (106) during the disengagement phase;

the cam mechanism (114) comprising at least one control surface (120, 122) produced on an internal wall of the cylinder body (56);

the elastic assistance element (106) being an axial compression elastic element interposed axially between a cup (108) and an abutment surface (110) fixed with respect to the assistance cylinder body (56), the cam mechanism (114) comprising at least one movable roller (116, 118) which travels over the control surface (120, 122) between an upstream position and a downstream position corresponding respectively to the upstream and downstream positions of the assistance piston (32);

the movable roller (116, 118) connected by a first connecting rod (124) to the piston (32) by a second connecting rod (126) to the cup (108);

the axis by which the connecting rods (124, 126) pivot on the movable roller (116, 118) being concurrent with a rotation axis (A2) of the roller (116, 118);

the control surface (120, 122) comprising an upstream portion (134) inclined with respect to the sliding axis (A1) and a downstream portion (136) substantially parallel to the sliding axis (A1) so that, during a first part of the disengagement phase, the movable roller (116, 118) moving first of all on the inclined portion (134) towards the sliding axis (A1) and in the downstream direction, from the upstream position thereof, transmitting part of the relaxation force of the elastic assistance element (106) to the assistance piston (32), by a step-down effect, and then, during a second part of the disengagement phase, the movable roller (116, 118) moving on the downstream portion (136) in the downstream direction, in the substantially axial direction, transmitting all the relaxation force of the elastic assistance element (106) to the assistance piston (32);

the distance between the pivot axes of the second connecting rod (126) being such that, in the upstream position of the movable roller (116, 118), the roller moving in the upstream direction beyond a point (B1) on the control surface (120, 122) where the second connecting rod (126) being perpendicular to the control surface (120, 122), so that the expansion force of the elastic assistance element (106) biasing the movement roller (116, 118) towards its upstream position;

the axial dimension of the elastic assistance element (106) in the relaxed state being less than the axial distance between the cup (108) and the associated fixed abutment surface (110), when the piston (32) occupies its downstream position, so as to eliminate the assistance force (Fa) during the end of the travel of the piston (32) in the downstream direction.

\* \* \* \* \*